United States Patent
Shih et al.

(10) Patent No.: US 10,548,324 B2
(45) Date of Patent: Feb. 4, 2020

(54) CERAMIC MATERIAL HAVING A POSITIVE SLOW RELEASE EFFECT, METHOD FOR MANUFACTURING THE SAME, AND SYSTEM COMPRISING THE SAME

(71) Applicant: KAOHSIUNG MEDICAL UNIVERSITY, Kaohsiung (TW)

(72) Inventors: Chi-Jen Shih, Kaohsiung (TW); Jung-Chang Kung, Kaohsiung (TW); Pei-Shan Lu, Kaohsiung (TW); Hao-Che Hsieh, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 12 days.

(21) Appl. No.: 15/842,211

(22) Filed: Dec. 14, 2017

(65) Prior Publication Data

US 2018/0368416 A1    Dec. 27, 2018

(30) Foreign Application Priority Data

Jun. 23, 2017  (TW) .................................. 106121156

(51) Int. Cl.
| | |
|---|---|
| *C04B 14/34* | (2006.01) |
| *A01N 59/16* | (2006.01) |
| *C04B 35/624* | (2006.01) |
| *C04B 38/00* | (2006.01) |

(52) U.S. Cl.
CPC .............. *A01N 59/16* (2013.01); *C04B 14/34* (2013.01); *C04B 35/624* (2013.01); *C04B 38/0051* (2013.01); *C04B 2235/40* (2013.01); *C04B 2235/428* (2013.01); *C04B 2235/96* (2013.01)

(58) Field of Classification Search
CPC .... A01N 59/16; A01N 25/08; C04B 38/0051; C04B 35/624; C04B 14/34; C04B 2235/428; C04B 2235/40; C04B 2235/96
See application file for complete search history.

(56) References Cited

FOREIGN PATENT DOCUMENTS

| CN | 103798289 A | 5/2014 |
|---|---|---|
| CN | 104368047 A | 2/2015 |

OTHER PUBLICATIONS

Ramay et al. Preparation of porous hydroxyapatite scaffolds by combination of the gel-casting and polymer sponge methods. Biomaterials 24 (2003) 3293-3302.*

(Continued)

*Primary Examiner* — Noah S Wiese
(74) *Attorney, Agent, or Firm* — Volpe and Koenig, P.C.

(57) ABSTRACT

The present disclosure discloses a ceramic material having a positive slow release effect and a method for manufacturing the same. The ceramic material comprises a hierarchically meso-macroporous structure which composition at least includes silicon and oxygen, wherein the hierarchically meso-macroporous structure includes a plurality of macropores and a wall having a plurality of arranged mesopores, and the plurality of macropores are separated by the wall; and nano-scale metal particles confined in at least one of the plurality of arranged mesopores. The nano-scale metal particles have a positive slow release effect from the at least one of the plurality of arranged mesopores. The ceramic material has a property of inhibiting growth of microorganisms or killing the microorganisms in an environment or a system containing a hydrophilic medium.

14 Claims, 13 Drawing Sheets

(56) References Cited

OTHER PUBLICATIONS

Patrascu et al. Composite Scaffolds Based on Silver Nanoparticles for Biomedical Applications. Journal of Nanomaterials vol. 2015, pp. 1-8.*
Long et al. Hierarchically nanostructured mesoporous carbonated hydroxyapatite microspheres for drug delivery systems with high drug-loading capacity. RSC Adv., 2013, 3, 24169.*
Gibson et al. Chemical characterization of silicon-substituted hydroxyapatite. J Biomed Mater Res. Mar. 15, 1999;44(4):422-8.*
Office Action issued in corresponding Taiwanese Patent Application No. 106121156 dated Mar. 31, 2018, consisting of 23 pp.

* cited by examiner

CERAMIC MATERIAL HAVING A POSITIVE SLOW RELEASE EFFECT, METHOD FOR MANUFACTURING THE SAME, AND SYSTEM COMPRISING THE SAME

CROSS-REFERENCE TO RELATED APPLICATION AND CLAIM OF PRIORITY

The present disclosure claims the right of priority based on Taiwan Patent Application Ser. No. 106121156, filed on Jun. 23, 2017, at the Taiwan Intellectual Property Office, the disclosure of which is incorporated herein in their entirety by reference.

FIELD OF THE DISCLOSURE

The present disclosure is related to a ceramic material and a method for manufacturing the same. In particular, the present disclosure is related to a ceramic material having a positive slow release effect and a property of inhibiting growth of microorganisms or killing the microorganisms in an environment or a system containing a hydrophilic medium.

BACKGROUND OF THE DISCLOSURE

Dr. Keiji Fukuda, Assistant Director-General for the World Health Organization, warned in 2014 that no new types of antibiotics have been developed in the past 30 years. Some pathogens have evolved to such an extent that existing antibiotics are helpless to resist them. Accordingly, it is urgent and necessary to develop new types of antibacterial agents. Currently, some international pharmaceutical companies have started to develop some new type materials with more potential. Biomedical material including nano-scale silver (Ag) particles is one of the most important development in this field.

Because the nano-scale Ag particles have high specific surface area and reactivity, the biomedical material including these particles is capable of inhibiting the growth of bacteria or viruses. With respect to this kind of the biomedical material, the diameter of the nano-scale Ag particles relates to the antibacterial effects, in which the diameter is preferably less than 10 nm. However, when the diameter of the nano-scale Ag particles is less than 10 nm, it has the problems of easily causing cytotoxicity to the organism, easily oxidizing, and easily causing aggregations resulted from the secondary bonding of the nano-scale Ag particles. In addition, the production capability of the colloidal silver product manufactured by the sol-gel technique presented in the market is small, the price of the product is high, and it cannot be effectively reused.

Therefore, the Applicant has disclosed a ceramic material having a positive slow release effect, a method for manufacturing the same, and a system comprising the same to improve the problems of the prior art mentioned above.

SUMMARY OF THE DISCLOSURE

In accordance with one aspect of the present disclosure provides a method for manufacturing a ceramic material having a hierarchically meso-macroporous structure and nano-scale metal particles, the method comprising steps of: providing and mixing raw materials or precursors thereof to form the hierarchically meso-macroporous structure which composition at least includes silicon and oxygen, a metal material or a precursor thereof, and a template surfactant of forming a mesoporous structure to form a mixture; synthesizing the mixture to form an initial gel by sol-gel technique; providing a three-dimensional macroporous configuration template; immersing the three-dimensional macroporous configuration template in the initial gel at least once; and removing the three-dimensional macroporous configuration template and the template surfactant of forming the mesoporous structure during a heat treatment at a temperature of no less than 400° C. to form the ceramic material.

In accordance with the other aspect of the present disclosure provides a ceramic material, comprising: a hierarchically meso-macroporous structure which composition at least includes silicon and oxygen, wherein the hierarchically meso-macroporous structure comprises a plurality of macropores and a wall having a plurality of arranged mesopores, and the plurality of macropores are separated by the wall; and nano-scale metal particles confined in at least one of the plurality of arranged mesopores, wherein the nano-scale metal particles have a positive slow release effect from the at least one of the plurality of arranged mesopores.

In accordance with another aspect of the present disclosure provides a system containing a hydrophilic medium and microorganisms of a first quantity A1 colony-forming unit (CFU), adding a ceramic material in the system, the microorganisms have a second quantity A2 CFU after a specific period of time, wherein the ceramic material comprising: a hierarchically meso-macroporous structure which composition at least includes silicon and oxygen, wherein the hierarchically meso-macroporous structure comprises a plurality of macropores and a wall having a plurality of arranged mesopores, and the plurality of macropores are separated by the wall; and nano-scale metal particles confined in at least one of the plurality of arranged mesopores, wherein the nano-scale metal particles have a positive slow release effect from the at least one of the plurality of arranged mesopores, wherein the A2 is no more than the A1.

The above objectives and advantages of the present disclosure will become more readily apparent to those ordinarily skilled in the art after reviewing the following detailed descriptions and accompanying drawings, in which:

DETAILED DESCRIPTION OF THE EMBODIMENTS

Figure 1A:
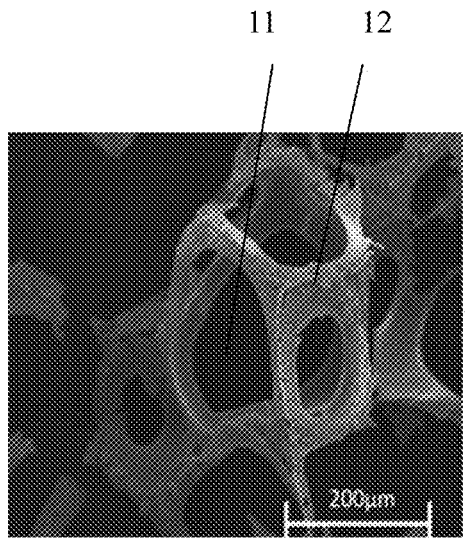
FIG. 1A is a scanning electron microscopy image of a ceramic material comprising a hierarchically meso-macroporous structure in accordance with a first embodiment of the present disclosure.

The present disclosure will now be described more specifically with reference to the following embodiments. It is to be noted that the following descriptions of embodiments of the present disclosure are presented herein for the purposes of illustration and description only; they are not intended to be exhaustive or to be limited to the precise form disclosed.

The present disclosure provides a ceramic material, wherein the ceramic material comprises a hierarchically meso-macroporous structure which composition at least includes silicon and oxygen, the hierarchically meso-macroporous structure comprises a plurality of macropores and a wall having a plurality of arranged mesopores, and the plurality of macropores are separated by the wall; and nano-scale metal particles confined in at least one of the plurality of arranged mesopores, wherein the nano-scale metal particles have a positive slow release effect from the at least one of the plurality of arranged mesopores and a property of inhibiting growth of microorganisms or killing the microorganisms.

The present disclosure provides a ceramic material having a biocompatibility, and the ceramic material is nontoxic to cells or tissues of an organism using ISO 10993-5 as an evaluation standard.

The present disclosure provides a ceramic material, wherein the hierarchically meso-macroporous structure further comprises one selected from a group consisting of phosphor, calcium and a combination thereof, and the ceramic material has a tissue induction property or a tissue conduction property.

The present disclosure provides a ceramic material, wherein the positive slow release effect of the nano-scale metal particles is defined as a concentration of the nano-scale metal particles releasing positively metal ions of at least 2 ppm within one hour and the metal ions keep releasing continuously for a period of at least 24 hours at room temperature when the ceramic material is located in an environment or a system containing a hydrophilic medium. The hydrophilic medium can be a biological body fluid, a water-containing solution, an alcohol, a human blood, a de-ionized water, a microbiological culture medium (Agar), a simulated body fluid, or combinations thereof. The environment or the system can be a biological cell, a biological tissue, a biological organ, a cosmetic, a drug, a medical device, or a biomedical material.

The present disclosure provides a ceramic material, wherein the nano-scale metal particles have a diameter of no more than 10 nm. The nano-scale metal particles can be one of gold, silver, copper, zinc, or combinations thereof, or one of metals having a property of inhibiting growth of microorganisms or killing the microorganisms.

The present disclosure provides a method for manufacturing a ceramic material containing nano-scale metal particles, the method comprises steps of providing and mixing raw materials or precursors thereof to form a hierarchically meso-macroporous structure which composition at least includes silicon and oxygen, a metal material or a precursor thereof, and a template surfactant of forming a mesoporous structure to form a mixture; synthesizing the mixture to form an initial gel by sol-gel technique; providing a three-dimensional macroporous configuration template; immersing the three-dimensional macroporous configuration template in the initial gel at least once; and removing the three-dimensional macroporous configuration template and the template surfactant of forming the mesoporous structure during a heat treatment at a temperature of no less than 400° C. to form the ceramic material.

The present disclosure provides a method for manufacturing a ceramic material containing nano-scale metal particles, the method further comprises a step of providing a stabilizer in the mixture to reduce an aggregation or oxidization possibility of the metal material or the precursor thereof.

The present disclosure provides a method for manufacturing a ceramic material containing nano-scale metal particles, wherein the ceramic material has a hierarchically meso-macroporous structure.

The present disclosure provides a method for manufacturing a ceramic material containing nano-scale metal particles, wherein the nano-scale metal particles have a positive slow release effect, and the positive slow release effect of the nano-scale metal particles is defined as a concentration of the nano-scale metal particles releasing positively metal ions of at least 2 ppm within one hour and the metal ions keep releasing continuously for a period of at least 24 hours at room temperature when the ceramic material is located in an environment or a system containing a hydrophilic medium. Wherein the hydrophilic medium can be a biological body fluid, a water-containing solution, an alcohol, a human blood, a de-ionized water, a microbiological culture medium (Agar), a simulated body fluid, or combinations thereof. Wherein the environment or the system can be a biological cell, a biological tissue, a biological organ, a cosmetic, a drug, a medical device, or a biomedical material.

The present disclosure provides a system containing a hydrophilic medium and microorganisms of a first quantity A1 colony-forming unit (CFU), adding a ceramic material in the system, the microorganisms have a second quantity A2 CFU after a specific period of time. The specific period of time is no more than 4 hours. The ceramic material comprises a hierarchically meso-macroporous structure which composition at least includes silicon and oxygen, wherein the hierarchically meso-macroporous structure comprises a plurality of macropores and a wall having a plurality of arranged mesopores, and the plurality of macropores are separated by the wall; and nano-scale metal particles confined in at least one of the plurality of arranged mesopores and having a positive slow release effect, wherein the A2 is no more than the A1. When A2 equals to A1, it represents that the ceramic material added thereto has a property of inhibiting growth of the microorganisms; and when A2 is less than A1, it represents that the ceramic material added thereto has a property of killing the microorganisms.

Figure 1B:
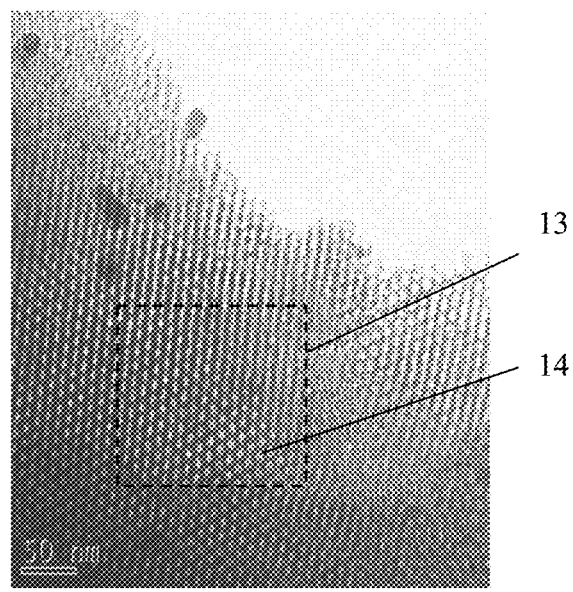
FIG. 1B is a partially enlarged image of FIG. 1A in accordance with the present disclosure.

First Embodiment:

FIG. 1A is a scanning electron microscopy image of a ceramic material comprising a hierarchically meso-macroporous structure in accordance with a first embodiment of the present disclosure, and FIG. 1B is a partially enlarged image of FIG. 1A in accordance with the present disclosure. The first embodiment discloses a ceramic material having a hierarchically meso-macroporous structure and one or more nano-scale metal particles, wherein the hierarchically meso-macroporous structure which composition includes silicon and oxygen. A ceramic material and the method for manufacturing the ceramic material of the first embodiment are completely described in detail by referring to FIGS. 1A-4. The present disclosure discloses a ceramic material. The ceramic material has a hierarchically meso-macroporous structure 1. The hierarchically meso-macroporous structure 1 is composed of a wall 12 and a plurality of macropores 11 having a pore diameter of 200-700 μm, and the plurality of macropores 11 are separated by the wall 12. The wall 12 is formed of a plurality of arranged mesopores 13, and at least one of the plurality of arranged mesopores has a pore diameter of 2-20 nm. One or more nano-scale metal particles 14 are confined in at least one of the plurality of arranged mesopores 13, as shown in FIGS. 1A-1B. The material of the one or more nano-scale metal particles 14 can be one selected from a group consisting of gold, silver, copper, zinc, and combinations thereof, or can be one or more metal particles having a property of inhibiting growth of the microorganisms or killing the microorganisms.

The ceramic material of the first embodiment is located in an environment or a system containing a hydrophilic medium at room temperature. On a condition that the material of the one or more nano-scale metal particles 14 is silver (Ag), the one or more nano-scale Ag particles have a positive slow release effect from the at least one of the plurality of arranged mesopores 13. The positive slow release effect of the nano-scale Ag particles is defined as a concentration of the nano-scale Ag particles releasing positively Ag ions of at least 2 ppm within one hour and the Ag ions keep releasing continuously for a period of at least 24 hours. Accordingly, the one or more nano-scale Ag particles 14 have a property of inhibiting growth of the microorganisms or killing the microorganisms in the ceramic material. The mechanism of the positive slow release effect can be separated into two stages. In the first stage, the one or more nano-scale Ag particles 14 adsorbed on the surfaces of the plurality of arranged mesopores 13 will release Ag ions in an environment or a system containing a hydrophilic medium. When the concentration of the Ag ions achieves the saturation concentration, the Ag ions will nucleate and grow to form nano-scale Ag particles. The nano-scale Ag particles and the dissociated Ag ions which do not form the nano-scale Ag particles can destruct a cell wall of the microorganisms or form reactive oxygen species (ROS) to destruct a structure of the microorganisms, which shows that the nano-scale Ag particles and the Ag ions have the property of inhibiting growth of the microorganisms or killing the microorganisms. After the nano-scale Ag particles 14 are fully oxidized, they will lose activity and therefore have no property of inhibiting growth of the microorganisms or killing the microorganisms. In the second stage, the nano-scale Ag particles 14 confined in the arranged mesopores 13 will release Ag ions in an environment or a system containing a hydrophilic medium, and the mechanism same as the first stage will repeat. The property of inhibiting growth of the microorganisms or killing the microorganisms in these two stages will last at least 24 hours.

The present disclosure provides a method for manufacturing a ceramic material having a hierarchically meso-macroporous structure 1 and nano-scale metal particles, the method comprises steps of providing and mixing raw materials or precursors thereof to form the hierarchically meso-macroporous structure 1 which composition at least includes silicon and oxygen, a metal material or a precursor thereof, and a template surfactant of forming a mesoporous structure to form a mixture; synthesizing the mixture to form an initial gel by sol-gel technique; providing a three-dimensional macroporous configuration template; immersing the three-dimensional macroporous configuration template in the initial gel at least once; and removing the three-dimensional macroporous configuration template and the template surfactant of forming the mesoporous structure during a heat treatment at a temperature of no less than 400° C. to form the ceramic material. The precursor of the raw material including silicon can be tetraethyl orthosilicate. When the metal material or the precursor thereof includes silver, the precursor of the metal material can be silver nitrate. The template surfactant of forming the mesoporous structure can be a thermal reversible hydrocolloid, Pluronic F-127. The three-dimensional macroporous configuration template can be a porous organism such as a natural sponge, or a synthetic porous object such as a polyurethane foam or a macroporous polylactic acid configuration formed by a three-dimensional printing technique. When a total quantity of the raw materials or the precursors thereof to form the hierarchically meso-macroporous structure is $M_1$ mole and a quantity of the metal material or the precursor thereof is $M_{metal}$ mole, the $M_{metal}$ is 0-10% of the $M_1$. Preferably, the $M_{metal}$ is 1% of the M1. In the other embodiment in accordance with the present disclosure, when the material of the nano-scale metal particles or the precursors thereof includes gold, the precursor thereof can be tetrachloroauric acid ($HAuCl_4$). When the material of the nano-scale metal particles or the precursors thereof includes copper, the precursor thereof can be copper nitrate or copper acetate. When the material of the nano-scale metal particles or the precursors thereof includes zinc, the precursor thereof can be zinc nitrate or zinc acetate. Definitely, any kind of metal material or the precursor thereof suitable therefor is within the scopes of the present disclosure, and is not limited to the ones described above.

In another embodiment, 0-10 mol % of silver was added into the ceramic material having a hierarchically meso-macroporous structure. In the subsequent descriptions, MS, MS-Ag1 and MS-Ag10 respectively represent the ceramic material with 0, 1 mol % and 10 mol % of silver, in which the molar ratios of Si:Ag are 100:0 for MS, 99:1 for MS-Ag1 and 90:10 for MS-Ag10 respectively.

In another embodiment, the method further comprises a step of providing a stabilizer in the mixture to reduce an aggregation or oxidization possibility of the metal material or the precursor thereof.

In the first embodiment, the obtained ceramic materials were sent to the biocompatibility test, such as an MTT assay, and were evaluated using ISO 10993-5:2009 as the evaluation standard. The test samples were cultivated with test cells for 24 hours. If the cell viability rate of the test cells is larger than 80% after 24-hour cultivation, it represents that the test samples are non-cytotoxic to the test cells. In addition to the test samples of the ceramic materials MS and MS-Ag1 in the first embodiment, 10% of dimethyl sulfoxide (DMSO) and de-ionized water were used as the control groups and were represented by Control (+) and Control (−) respectively.

The culture medium used for the biocompatibility test was formed by first sterilizing MS and MS-Ag1 with high temperature and high pressure at a concentration of the extract solution in a ratio of 10 of the weight (in mg) of the ceramic material to the volume (in ml) of each specific cell culture medium. After placing in an incubator at constant temperature of 37° C. for 24 hours, the solution was centrifuged at 5000 rpm for 10 minutes. The supernatant was drew and taken as the extract solution of the test sample. The cell culture medium was a Dulbecco's modified Eagle's medium (DMEM) containing 10% of bovine serum (BS) and 1% of penicillin/streptomycin. The test cells chosen were the macrophages RAW264.7, the mast cells RBL-2H3 and the fibroblast cells NIH/3T3. The test cells and the cell culture medium were mixed and added into a 96-well microtiter plate with the number of the test cells of $1 \times 10^5$ cells/100 μL. After placing in an incubator for 24 hours, the supernatant in the 96-well microtiter plate was removed, and the aforementioned extract solution of the test sample was added to each well to achieve an aqueous volume of 100 μL per well as the culture medium. After culturing the test cells for 24 hours, 50 μL of 3-(4,5-cimethylthiazol-2-yl)-2,5-diphenyl tetrazolium bromide was added for MTT assay. After placing in a 5% $CO_2$ incubator at 37° C. for 4 hours, the sample in each well was measured for the absorbance (or called the optical density (OD) value) at a wavelength of 600 nm ($OD_{600}$ value) by using an enzyme-linked immunosorbent assay (ELISA) reader, and the cell viability rate of the test cells was calculated accordingly.

Figure 2:
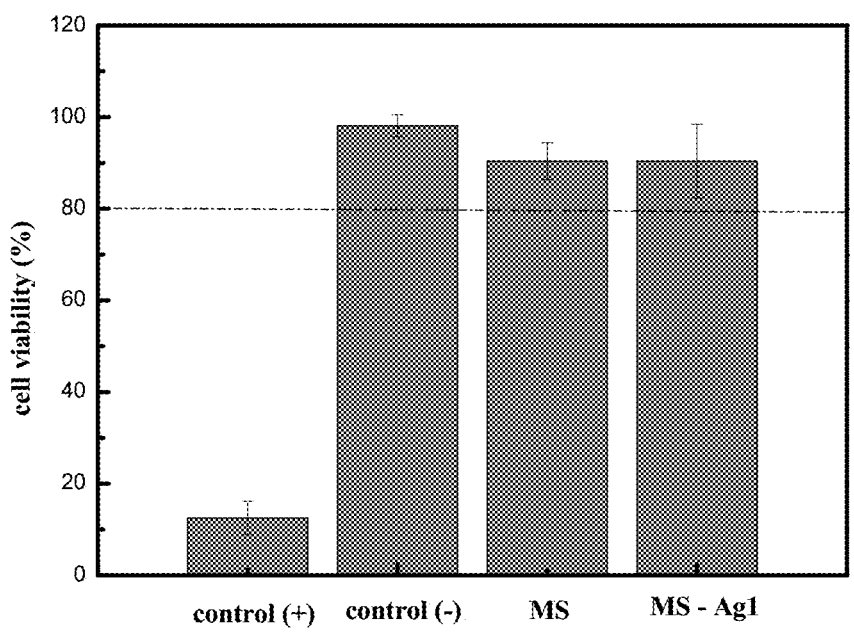
FIG. 2 is a diagram of a statistical result showing a biocompatibility test for a ceramic material sample to the macrophages RAW264.7 in accordance with the first embodiment of the present disclosure.
Figure 3:
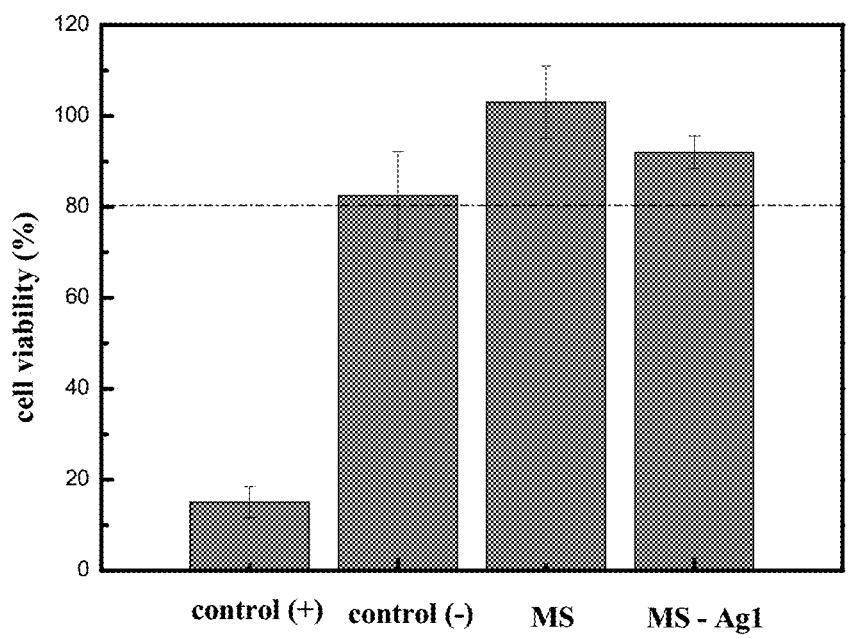
FIG. 3 is a diagram of a statistical result showing a biocompatibility test for a ceramic material sample to the mast cells RBL-2H3 in accordance with the first embodiment of the present disclosure.
Figure 4:
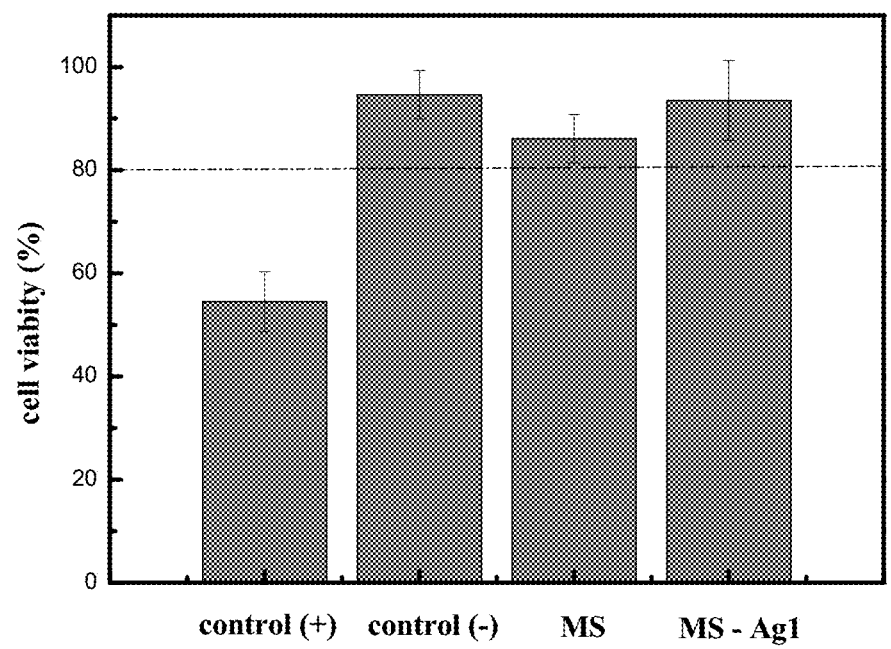
FIG. 4 is a diagram of a statistical result showing a biocompatibility test for a ceramic material sample of to the fibroblast cells NIH/3T3 in accordance with the first embodiment of the present disclosure.

The test results of the biocompatibility for the ceramic materials in accordance with the first embodiment are shown as the statistical diagrams in FIGS. 2-4. FIG. 2 is a diagram of a statistical result showing the biocompatibility test for a ceramic material sample to the macrophages RAW264.7 in accordance with f the first embodiment of the present disclosure, FIG. 3 is a diagram of a statistical result showing the biocompatibility test for a ceramic material sample to the mast cells RBL-2H3 in accordance with the first embodiment of the present disclosure, and FIG. 4 is a diagram of a statistical result showing the biocompatibility test for a ceramic material sample to the fibroblast cells NIH/3T3 in accordance with the first embodiment of the present disclosure. As the result of the biocompatibility test shown in FIG. 2, the cell viability rate of each of MS and MS-Ag1 to the macrophages RAW264.7 could reach 90%, which represented non-cytotoxicity to the test cells. As the result of the biocompatibility test shown in FIG. 3, the cell viability rate of each of MS and MS-Ag1 to the mast cells RBL-2H3 could reach 90-100%, which represented non-cytotoxicity to the test cells. As the result of the biocompatibility test shown in FIG. 4, the cell viability rate of each of MS and MS-Ag1 to the fibroblast cells NIH/3T3 could be larger than 85%, which represented non-cytotoxicity to the test cells. Therefore, the ceramic materials used in the first embodiment were biocompatible.

Second Embodiment:

The second embodiment of the present disclosure discloses a ceramic material comprising a hierarchically meso-macroporous structure and having a tissue induction property or a tissue conduction property. The ceramic material can be used for a bone filling or a bone integration material. The bone filling or bone integration material is composed of silicon, calcium, phosphor, and oxygen. A ceramic material and the method for manufacturing the ceramic material of the second embodiment are completely described in detail by referring to FIGS. 5-21. The present disclosure discloses a ceramic material. The ceramic material has the hierarchically meso-macroporous structure similar to that of the hierarchically meso-macroporous structure 1 shown in FIGS. 1A-1B. The hierarchically meso-macroporous structure is composed of a wall 12 and a plurality of macropores 11 having a pore diameter of 200-700 μm, and a plurality of macropores 11 are separated by the wall 12. The wall 12 is formed of a plurality of arranged mesopores 13, and at least one of the plurality of arranged mesopores has a pore diameter of 2-20 nm. The one or more nano-scale metal particles 14 are confined in at least one of the plurality of arranged mesopores 13, as referred to FIGS. 1A-1B.

The ceramic material of the second embodiment was located in an environment or a system containing a hydrophilic medium at room temperature. On a condition that the material of the one or more nano-scale metal particles is silver (Ag), the one or more nano-scale Ag particles have a positive slow release effect from the at least one of the plurality of arranged mesopores. The positive slow release effect of the nano-scale Ag particles is defined as a concentration of the nano-scale Ag particles releasing positively Ag ions of at least 2 ppm within one hour and the Ag ions keep releasing continuously for a period of at least 24 hours. Accordingly, the one or more nano-scale Ag particles have a property of inhibiting growth of the microorganisms or killing the microorganisms. The mechanism of the positive slow release effect was similar to that described in the first embodiment.

The present disclosure provides a method for manufacturing a ceramic material having a hierarchically meso-macroporous structure and nano-scale metal particles, the method comprises steps of providing and mixing raw materials or precursors thereof to form the hierarchically meso-macroporous structure which composition includes silicon, oxygen, phosphor and oxygen, a metal material or a precursor thereof, and a template surfactant of forming a mesoporous structure to form a mixture; synthesizing the mixture to form an initial gel by sol-gel technique; providing a three-dimensional macroporous configuration template; immersing the three-dimensional macroporous configuration template in the initial gel at least once; and removing the three-dimensional macroporous configuration template and the template surfactant of forming a mesoporous structure during a heat treatment at a temperature of no less than 400° C. to form the ceramic material. The precursor of the raw material including silicon can be tetraethyl orthosilicate. The precursor of the raw material including calcium can be calcium nitrate tetrahydrate. The precursor of the raw material including phosphor can be triethyl phosphate. When the metal material or the precursor thereof includes silver, the precursor of the metal material can be silver nitrate. The template surfactant of forming a mesoporous structure can be a thermal reversible hydrocolloid, Pluronic F-127. The three-dimensional macroporous configuration template can be a porous organism, such as a natural sponge or a synthetic porous object, such as a polyurethane foam or a macroporous polylactic acid configuration formed by a three-dimensional printing technique. When a total quantity of the raw materials or the precursors thereof to form the hierarchically meso-macroporous structure is $M_1$ mole and a quantity of the metal material or the precursor thereof is $M_{metal}$ mole, the $M_{metal}$ is 0-10% of the $M_1$. Preferably, the $M_{metal}$ is 1% of the M1. In the other embodiment in accordance with the present disclosure, when the material of the nano-scale metal particles or the precursors thereof includes gold, the precursor thereof can be tetrachloroauric acid ($HAuCl_4$). When the material of the nano-scale metal particles or the precursors thereof includes copper, the precursor thereof can be copper nitrate or copper acetate. When the material of the nano-scale metal particles or the precursors thereof includes zinc, the precursor thereof can be zinc nitrate or zinc acetate. Definitely, any kind of metal material or the precursor thereof suitable therefor is within the scopes of the present disclosure, and is not limited to the ones described above.

In another embodiment, 0-10 mol % of silver was added into the ceramic material having a hierarchically meso-macroporous structure. In the subsequent descriptions, MBG, MBG-Ag1, MBG-Ag3, MBG-Ag5 and MBG-Ag10 respectively represent the ceramic material with 0, 1 mol %, 3 mol %, 5 mol % and 10 mol % of silver, in which the molar ratios of Si:Ca:P:Ag are 80:15:5:0 for MBG, 79:15:5:1 for MBG-Ag1, 77:15:5:3 for MBG-Ag3, 75:15:5:5 for MBG-Ag5 and 70:15:5:10 for MBG-Ag10 respectively.

In another embodiment, the ceramic material having a hierarchically meso-macroporous structure is a powder form that can be immersed, diluted or reused, and a specific surface area of the powder form is in the range of 300-700 $m^2/g$.

Figure 5:
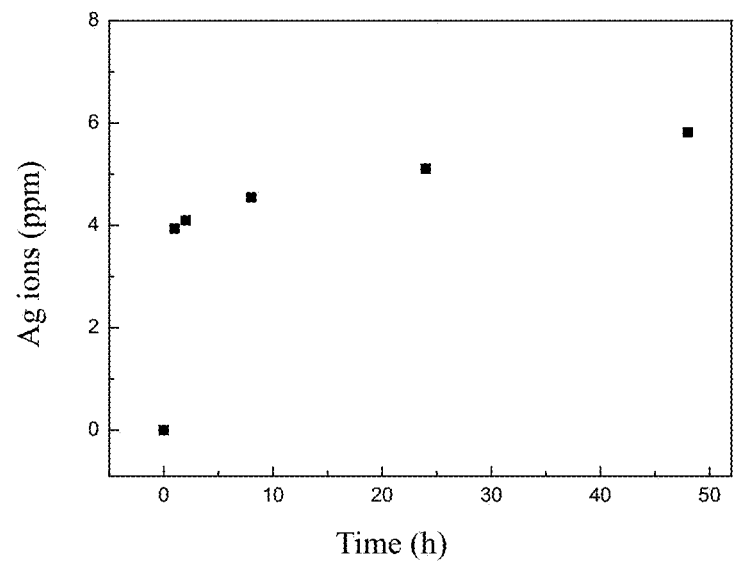
FIG. 5 is a diagram showing Ag ions release rate from the ceramic material MBG-Ag1 in an environment of the deionized water in accordance with a second embodiment of the present disclosure.
Figure 6:
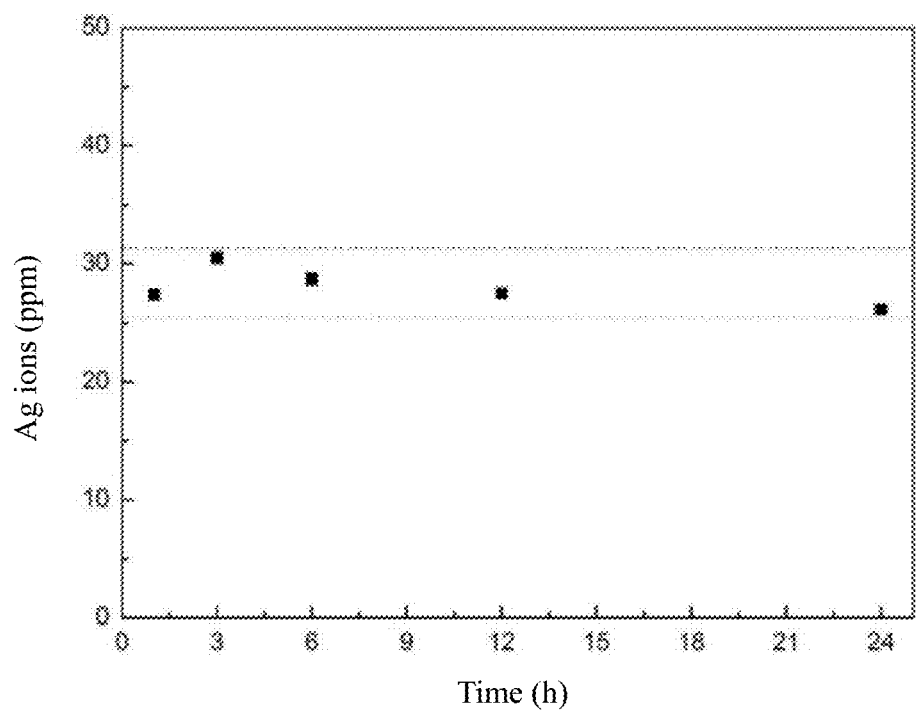
FIG. 6 is a diagram showing Ag ions release rate from the ceramic material MBG-Ag1 in an environment of the tryptic soy broth (TSB) in accordance with the second embodiment of the present disclosure.

In another embodiment, the silver ions release rate of the MBG-Ag 1 in an environment containing a hydrophilic medium was measured by using an inductively coupled plasma mass spectrometry (ICP-MS) to verify that the nano-scale metal particles contained therein have a positive slow release effect. FIG. 5 is a diagram showing Ag ions release rate from the ceramic material MBG-Ag1 in the environment of the de-ionized water in accordance with the second embodiment of the present disclosure, and FIG. 6 is a diagram showing Ag ions release rate from the ceramic material MBG-Ag1 in the environment of the tryptic soy broth (TSB) in accordance with the second embodiment of the present disclosure. As shown in FIG. 5, the MBG-Ag1 positively released the Ag ions in the de-ionized water at the testing time of 1, 2, 8, 24, and 48 hours are in the concentrations of 3.94, 4.10, 4.55, 5.11 and 5.82 mg/L respectively. As shown in FIG. 6, the MBG-Ag1 positively released the Ag ions in the tryptic soy broth at the testing time of 1 hour is in a concentration of 26 mg/L, and kept releasing the Ag ions at least for 24 hours. It could be seen that, the nano-scale metal particles contained in the ceramic material of the second embodiment have a positive slow release effect in an environment or a system containing a hydrophilic medium, and the release rate of the metal ions in different hydrophilic mediums are different.

In another embodiment, a time-kill curves test was performed to verify that the nano-scale metal particles contained in the ceramic material having a hierarchically meso-macroporous structure and located in an environment or a system containing a hydrophilic medium have a positive slow release effect, and the nano-scale Ag particles in the ceramic material had the ability to inhibit growth of microorganisms or kill the microorganisms. This test was performed in an environment or a system having a hydrophilic medium possessing the microorganisms, such as a liquid culture medium, at a temperature of 37° C. with or without the addition of the ceramic material having a hierarchically meso-macroporous structure of the second embodiment. After a specific cultivation time, each group of the solutions were formed, and the numbers of the microorganisms in each group were measured. The numbers of the microorganisms were calculated by measuring the turbidity of each group of the solutions. The turbidity of each solution was obtained by measuring the absorbance (or called the optical density (OD) value) at a wavelength of 600 nm ($OD_{600}$ value) using the ELISA reader. The growth curves of the test microorganisms in the environment or system were plotted with time as the horizontal axis and the optical density at 600 nm ($OD_{600}$) as the longitudinal axis. The test microorganisms can be selected from bacteria, viruses, fungi, or protozoa, wherein the bacteria can be such as Methicillin-resistant *staphylococcus aureus*, *Staphylococcus aureus*, *Pseudomonas aeruginosa*, *Escherichia coli*, *Aggregatibacter actinomycetemcomitans*, *Candida albicans*, *Klebsiella pneumoniae*, *Enterococcus faecalis*, and so on. The fungi can be such as *Aspergillus niger*. The conditions of the liquid culture medium included the following: MBG-Ag1, MBG-Ag5 and MBG-Ag10 were respectively added in the extract solution having concentrations in ratios of 2.5, 5, 10 and 20 of the weight (in mg) of the ceramic material to the volume (in ml) of each specific culture medium, such as the tryptic soy broth (TSB). After placing in an incubator at a constant temperature of 37° C. and extracting at 160 rpm for 24 hours, the solution was centrifuged at 3000 rpm for 5 minutes. The supernatant was drew and taken as the extract solution of the test sample. The test microorganisms were thawed and inoculated on each specific agar, and then placed in an incubator at a specific temperature for a specific period of time, the strain was swabbed with a sterile cotton swab and inoculated into each sterilized liquid culture medium (agar). The specific period of time was no more than 4 hours. A turbidimeter was used to measure the test microorganism solution and the concentration was adjusted to about $1.5 \times 10^8$ CFU/mL. The test microorganism solution was added to the 96-well microtiter plate containing the prepared extract solution. After inoculation, the final concentration of the test microorganism solution was approximately $5 \times 10^5$ CFU/mL. After incubation at 37° C., the absorbance was measured once every hour until reaching 24 hours by using a spectrophotometer, and the time-kill curves were plotted to find out the minimum inhibitory concentration (MIC) of different microorganisms with respect to the ceramic material having a hierarchically meso-macroporous structure of the embodiment. The minimum inhibitory concentration (MIC) referred to the minimum concentration that could inhibit growth of the microorganisms and was observed after culturing for 24 hours. The condition of the control group included that a liquid culture medium containing different test strains was cultured for 24 hours without adding any test liquid formed of extract solution including the ceramic material having a hierarchically meso-macroporous structure, and this control group was represented by Control (–) in subsequent descriptions.

The results of the time-kill curves test are shown in FIGS. 7-21.

1. The Time-kill Curves Test for Methicillin-resistant *Staphylococcus aureus*

Figure 7:
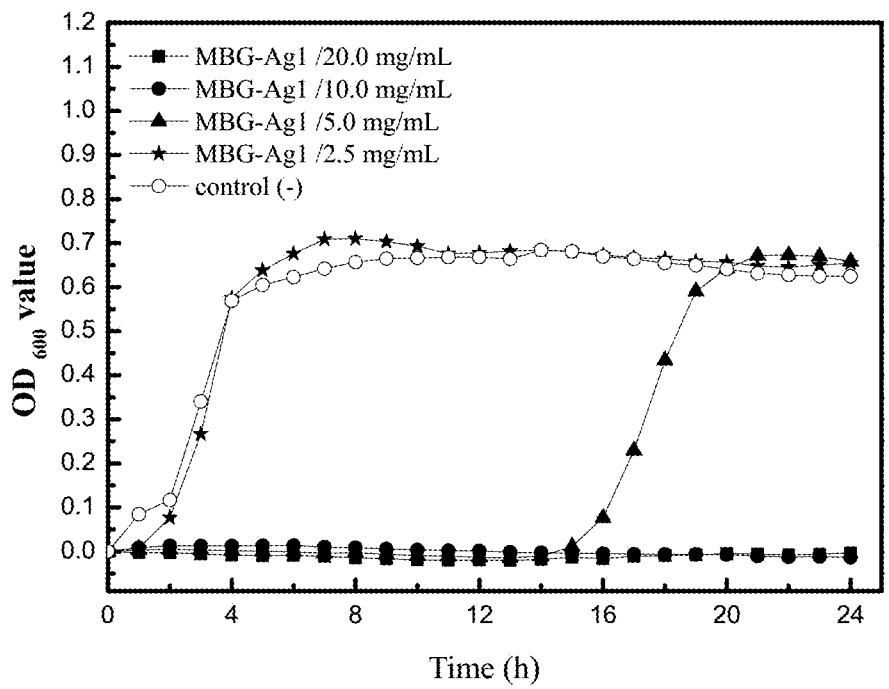
FIG. 7 is a diagram showing growth curves of time-kill curves test for Methicillin-resistant *Staphylococcus aureus* performed by adding different concentrations of the ceramic material MBG-Ag1 in a liquid culture medium in accordance with the second embodiment of the present disclosure.
Figure 8:
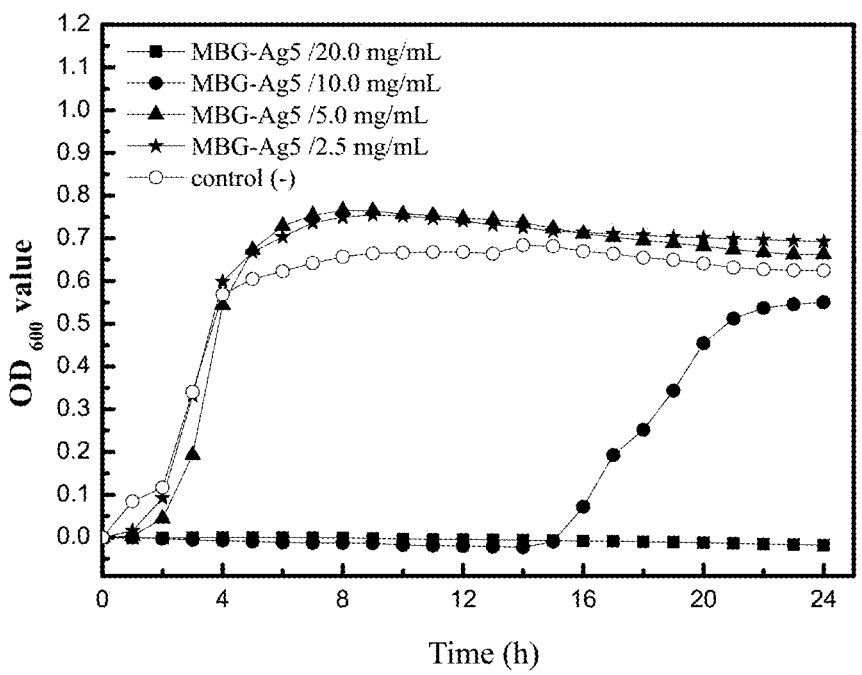
FIG. 8 is a diagram showing growth curves of time-kill curves test for Methicillin-resistant *Staphylococcus aureus* performed by adding different concentrations of the ceramic material MBG-Ag5 in a liquid culture medium in accordance with the second embodiment of the present disclosure.
Figure 9:
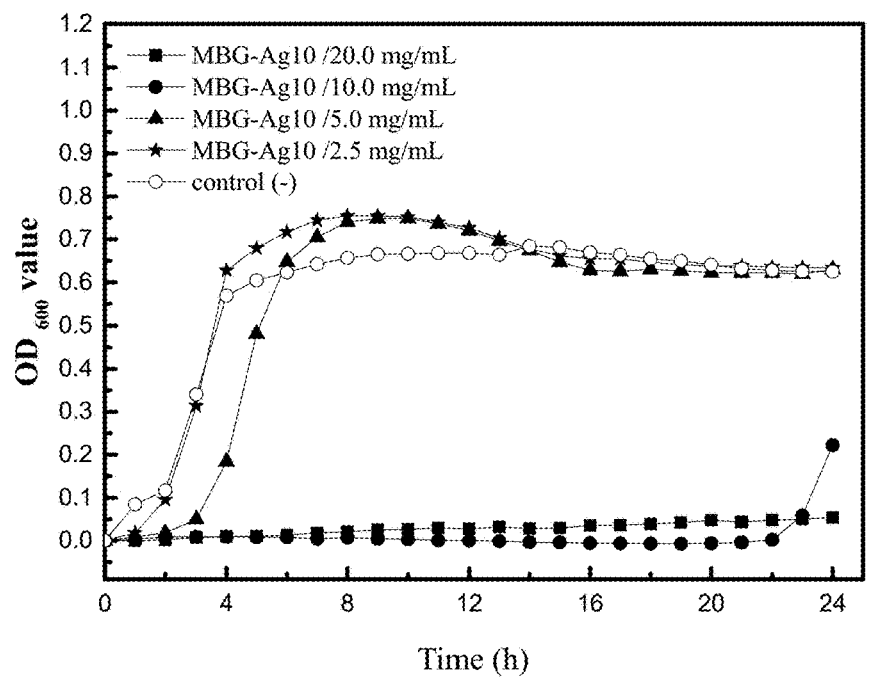
FIG. 9 is a diagram showing growth curves of time-kill curves test for Methicillin-resistant *Staphylococcus aureus* performed by adding different concentrations of the ceramic material MBG-Ag10 in a liquid culture medium in accordance with the second embodiment of the present disclosure.

FIGS. 7-9 show growth curves of time-kill curves test for Methicillin-resistant *Staphylococcus aureus* performed by adding different concentrations of the ceramic materials MBG-Ag1, MBG-Ag5 and MBG-Ag10 in a liquid culture medium in accordance with the second embodiment of the present disclosure. FIG. 7 is a diagram showing growth curves of time-kill curves test for Methicillin-resistant *Staphylococcus aureus* performed by adding different concentrations of the ceramic material MBG-Ag1 in a liquid culture medium in accordance with the second embodiment of the present disclosure. The condition to prepare the liquid culture medium included adding MBG-Ag1 in the extract solution having concentrations in ratios of 2.5, 5, 10 and 20 of the weight (in mg) of the ceramic material to the volume (in ml) of specific culture medium. It could be seen from FIG. 7 that, the extract solution had an excellent effect of inhibiting growth of the bacteria when the concentrations of MBG-Ag1 extract solution were 20 mg/mL and 10 mg/mL. The effect of inhibiting growth of the bacteria was limited when the concentration of the extract solution was 5 mg/mL, and there was a growth phenomenon of Methicillin-resistant *Staphylococcus aureus* at 16 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 8 is a diagram showing growth curves of time-kill curves test for Methicillin-resistant *Staphylococcus aureus* performed by adding different concentrations of the ceramic material MBG-Ag5 in a liquid culture medium in accordance with the second embodiment of the present disclosure. The condition to prepare the liquid culture medium included adding MBG-Ag5 in the extract solution having concentrations in ratios of 2.5, 5, 10 and 20 of the weight (in mg) of the ceramic material to the volume (in ml) of specific culture medium. It could be seen from FIG. 8 that, the extract solution had an excellent effect of inhibiting growth of the bacteria when the concentration of MBG-Ag5 extract solution was 20 mg/mL. The effect of inhibiting growth of the bacteria was limited when the concentration of the extract solution was 10 mg/mL, and there was a growth phenomenon of Methicillin-resistant *Staphylococcus aureus* at 16 hours. Therefore, the minimum inhibitory concentration (MIC) was expected in the range from 10 mg/mL to 20 mg/mL. No effect of inhibiting growth of the bacteria was observed when the concentration of the extract solution was 5 mg/mL or 2.5 mg/mL.

FIG. 9 is a diagram showing growth curves of time-kill curves test for Methicillin-resistant *Staphylococcus aureus* performed by adding different concentrations of the ceramic material MBG-Ag10 in a liquid culture medium in accordance with the second embodiment of the present disclosure. The condition to prepare the liquid culture medium included adding MBG-Ag10 in the extract solution having concentrations in ratios of 2.5, 5, 10 and 20 of the weight (in mg) of the ceramic material to the volume (in ml) of specific culture medium. It could be seen from FIG. 9 that, the extract solution had an excellent effect of inhibiting growth of the bacteria when the concentration of MBG-Ag10 extract solution was 20 mg/mL. The effect of inhibiting growth of the bacteria was limited when the concentration of the extract solution was 10 mg/mL, and there was a growth phenomenon of Methicillin-resistant *Staphylococcus aureus* at 23 hours. Therefore, the minimum inhibitory concentration (MIC) was expected in the range from 10 mg/mL to 20 mg/mL. No effect of inhibiting growth of the bacteria was observed when the concentration of the extract solution was 5 mg/mL or 2.5 mg/mL.

Preliminary conclusion: The effect of inhibiting growth of Methicillin-resistant *Staphylococcus aureus* provided by the ceramic materials of the second embodiment of the present disclosure was in the sequence of MBG-Ag1>MBG-Ag10>MBG-Ag5.

2. The Time-kill Curves Test for *Staphylococcus aureus* ATCC 6538

Figure 10:
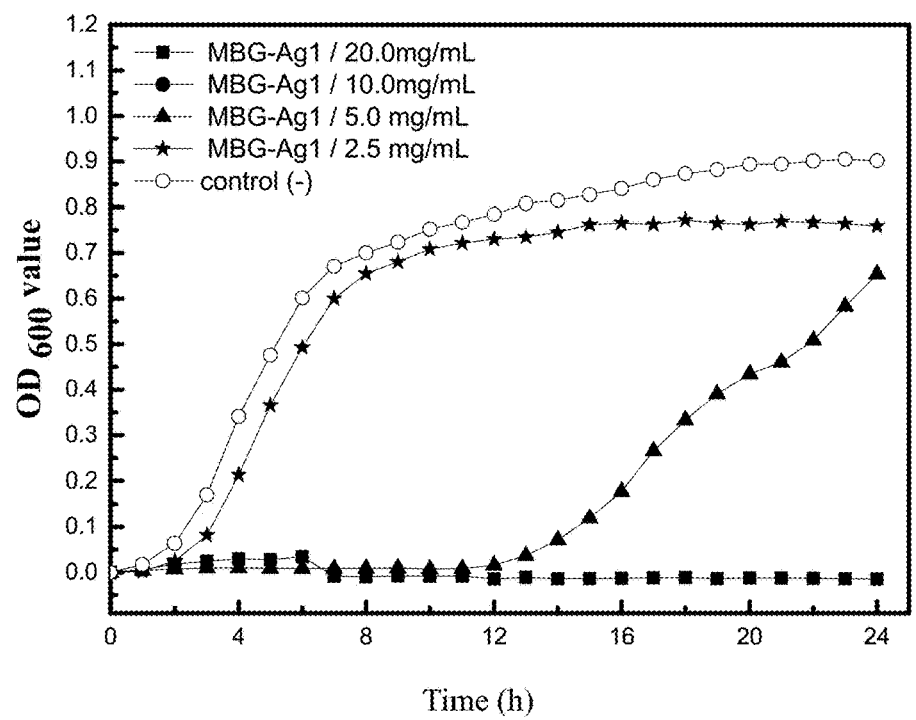
FIG. 10 is a diagram showing growth curves of time-kill curves test for *Staphylococcus aureus* performed by adding different concentrations of the ceramic material MBG-Ag1 in a liquid culture medium in accordance with the second embodiment of the present disclosure.
Figure 11:
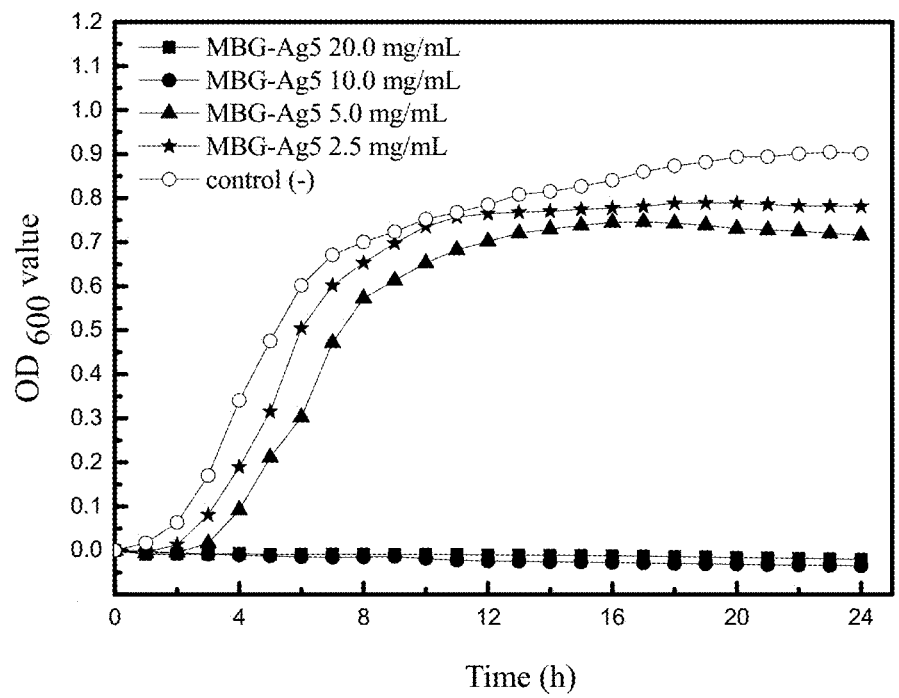
FIG. 11 is a diagram showing growth curves of time-kill curves test for *Staphylococcus aureus* performed by adding different concentrations of the ceramic material MBG-Ag5 in a liquid culture medium in accordance with the second embodiment of the present disclosure.
Figure 12:
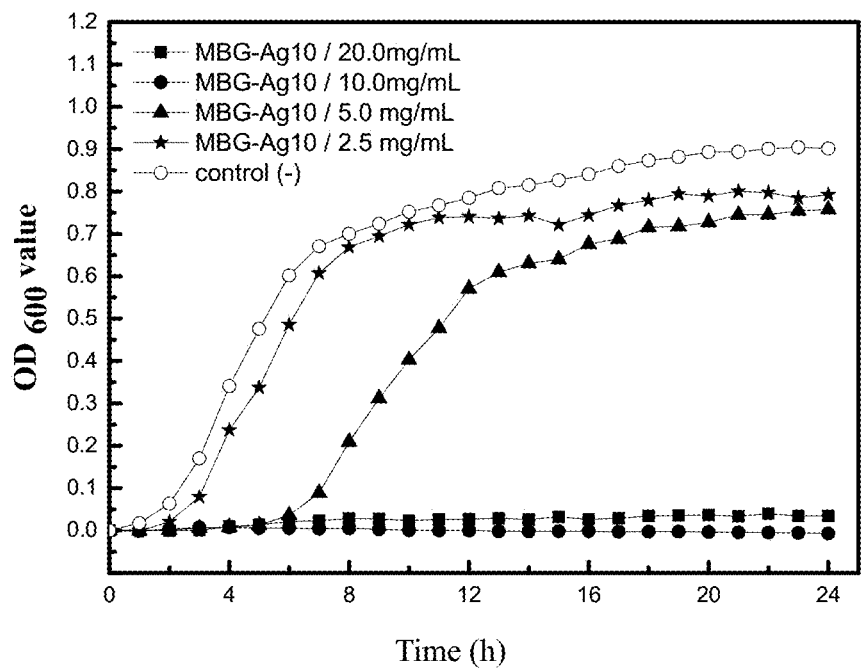
FIG. 12 is a diagram showing growth curves of time-kill curves test for *Staphylococcus aureus* performed by adding different concentrations of the ceramic material MBG-Ag10 in a liquid culture medium in accordance with the second embodiment of the present disclosure.

FIGS. 10-12 show growth curves of time-kill curves test for *Staphylococcus aureus* performed by adding different concentrations of the ceramic materials MBG-Ag1, MBG-Ag5 and MBG-Ag10 in a liquid culture medium in accordance with the second embodiment of the present disclosure. FIG. 10 is a diagram showing growth curves of time-kill curves test for *Staphylococcus aureus* performed by adding different concentrations of the ceramic material MBG-Ag1 in a liquid culture medium in accordance with the second embodiment of the present disclosure. The condition to prepare the liquid culture medium included adding MBG-Ag1 in the extract solution having concentrations in ratios of 2.5, 5, 10 and 20 of the weight (in mg) of the ceramic material to the volume (in ml) of specific culture medium. It could be seen from FIG. 10 that, the extract solution had an excellent effect of inhibiting growth of the bacteria when the concentrations of MBG-Ag1 extract solution were 20 mg/mL and 10 mg/mL. The effect of inhibiting growth of the bacteria was limited when the concentration of the extract solution was 5 mg/mL, and there was a growth phenomenon of *Staphylococcus aureus* at 13 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 11 is a diagram showing growth curves of time-kill curves test for *Staphylococcus aureus* performed by adding different concentrations of the ceramic material MBG-Ag5 in a liquid culture medium in accordance with the second embodiment of the present disclosure. The condition to prepare the liquid culture medium included adding MBG-Ag5 in the extract solution having concentrations in ratios of 2.5, 5, 10 and 20 of the weight (in mg) of the ceramic material to the volume (in ml) of specific culture medium. It could be seen from FIG. 11 that, the extract solution had an excellent effect of inhibiting growth of the bacteria when the concentrations of MBG-Ag5 extract solution were 20 mg/mL and 10 mg/mL. The effect of inhibiting growth of the bacteria was limited when the concentration of the extract solution was 5 mg/mL, and there was a growth phenomenon of *Staphylococcus aureus* at 4 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 12 is a diagram showing growth curves of time-kill curves test for *Staphylococcus aureus* performed by adding different concentrations of the ceramic material MBG-Ag10 in a liquid culture medium in accordance with the second embodiment of the present disclosure. The condition to prepare the liquid culture medium included adding MBG-Ag10 in the extract solution having concentrations in ratios of 2.5, 5, 10 and 20 of the weight (in mg) of the ceramic material to the volume (in ml) of specific culture medium. It could be seen from FIG. 12 that, the extract solution had an excellent effect of inhibiting growth of the bacteria when the concentrations of MBG-Ag10 extract solution were 20 mg/mL and 10 mg/mL. The effect of inhibiting growth of the bacteria was limited when the concentration of the extract solution was 5 mg/mL, and there was a growth phenomenon of *Staphylococcus aureus* at 7 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

Preliminary conclusion: The effect of inhibiting growth of *Staphylococcus aureus* provided by the ceramic materials of the second embodiment of the present disclosure was in the sequence of MBG-Ag1>MBG-Ag10>MBG-Ag5.

3. The Time-kill Curves Test for *Pseudomonas aeruginosa* ATCC 9027

Figure 13:
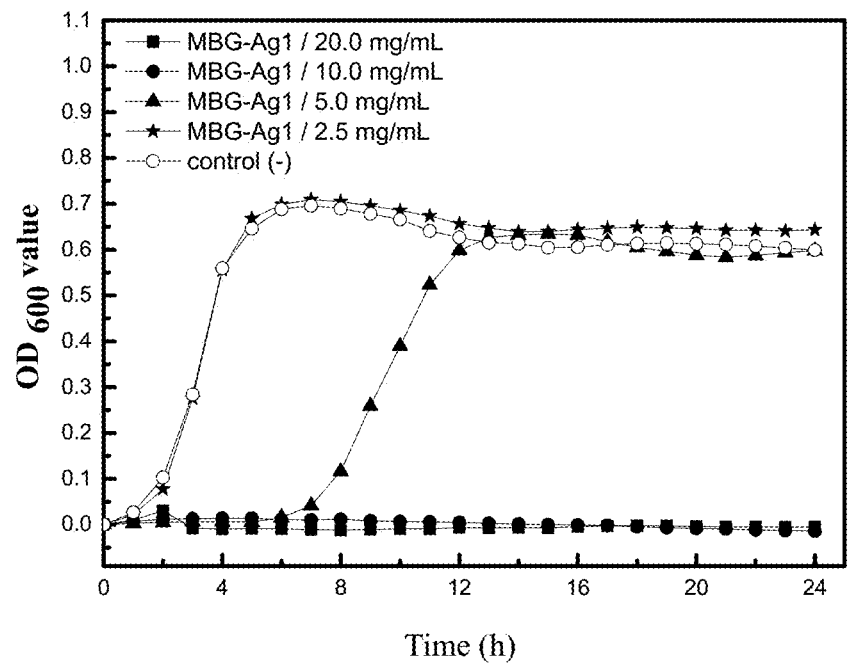
FIG. 13 is a diagram showing growth curves of time-kill curves test for *Pseudomonas aeruginosa* performed by adding different concentrations of the ceramic material MBG-Ag1 in a liquid culture medium in accordance with the second embodiment of the present disclosure.
Figure 14:
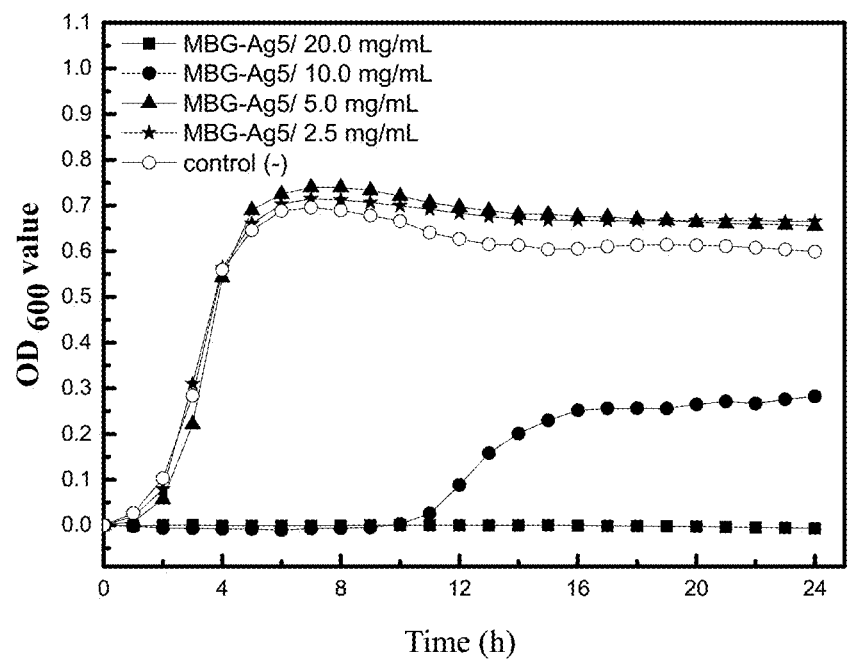
FIG. 14 is a diagram showing growth curves of time-kill curves test for *Pseudomonas aeruginosa* performed by adding different concentrations of the ceramic material MBG-Ag5 in a liquid culture medium in accordance with the second embodiment of the present disclosure.
Figure 15:
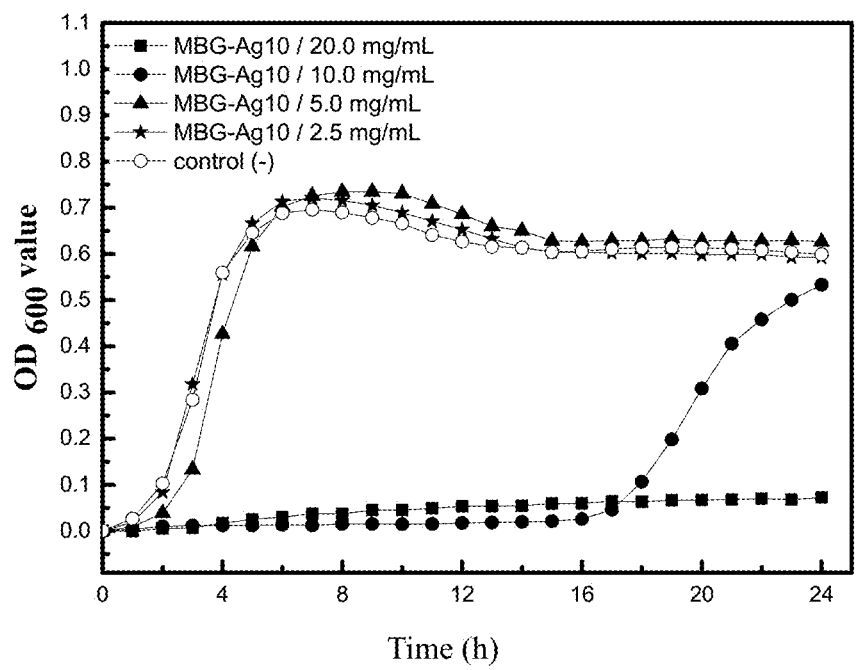
FIG. 15 is a diagram showing growth curves of time-kill curves test for *Pseudomonas aeruginosa* performed by adding different concentrations of the ceramic material MBG-Ag10 in a liquid culture medium in accordance with the second embodiment of the present disclosure.

FIGS. 13-15 show growth curves of time-kill curves test for *Pseudomonas aeruginosa* performed by adding different concentrations of the ceramic materials MBG-Ag1, MBG-Ag5 and MBG-Ag10 in a liquid culture medium in accordance with the second embodiment of the present disclosure. FIG. 13 is a diagram showing growth curves of time-kill curves test for *Pseudomonas aeruginosa* performed by adding different concentrations of the ceramic material MBG-Ag1 in a liquid culture medium in accordance with the second embodiment of the present disclosure. The condition to prepare the liquid culture medium included adding MBG-Ag1 in the extract solution having concentrations in ratios of 2.5, 5, 10 and 20 of the weight (in mg) of the ceramic material to the volume (in ml) of specific culture medium. It could be seen from FIG. 13 that, the extract solution had an excellent effect of inhibiting growth of the bacteria when the concentrations of MBG-Ag1 extract solution were 20 mg/mL and 10 mg/mL. The effect of inhibiting growth of the bacteria was limited when the concentration of the extract solution was 5 mg/mL, and there was a growth phenomenon of *Pseudomonas aeruginosa* at 7 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 14 is a diagram showing growth curves of time-kill curves test for *Pseudomonas aeruginosa* performed by adding different concentrations of the ceramic material MBG-Ag5 in a liquid culture medium in accordance with the second embodiment of the present disclosure. The condition to prepare the liquid culture medium included adding MBG-Ag5 in the extract solution having concentrations in ratios of 2.5, 5, 10 and 20 of the weight (in mg) of the ceramic material to the volume (in ml) of specific culture medium. It could be seen from FIG. 14 that, the extract solution had an excellent effect of inhibiting growth of the bacteria when the concentration of MBG-Ag5 extract solution was 20 mg/mL. The effect of inhibiting growth of the bacteria was limited when the concentration of the extract solution was 10 mg/mL, and there was a growth phenomenon of *Pseudomonas aeruginosa* at 11 hours. Therefore, the minimum inhibitory concentration (MIC) was expected in the range from 10 mg/mL to 20 mg/mL. No effect of inhibiting growth of the bacteria was observed when the concentration of the extract solution was 5 mg/mL or 2.5 mg/mL.

FIG. 15 is a diagram showing growth curves of time-kill curves test for *Pseudomonas aeruginosa* performed by adding different concentrations of the ceramic material MBG-Ag10 in a liquid culture medium in accordance with the second embodiment of the present invention. The condition to prepare the liquid culture medium included adding MBG- Ag10 in the extract solution having concentrations in ratios of 2.5, 5, 10 and 20 of the weight (in mg) of the ceramic material to the volume (in ml) of specific culture medium. It could be seen from FIG. 15 that, the extract solution had an excellent effect of inhibiting growth of the bacteria when the concentration of MBG-Ag10 extract solution was 20 mg/mL. The effect of inhibiting growth of the bacteria was limited when the concentration of the extract solution was 10 mg/mL, and there was a growth phenomenon of *Pseudomonas aeruginosa* at 17 hours. Therefore, the minimum inhibitory concentration (MIC) was expected in the range from 10 mg/mL to 20 mg/mL. No effect of inhibiting growth of the bacteria was observed when the concentration of the extract solution was 5 mg/mL or 2.5 mg/mL.

Preliminary conclusion: The effect of inhibiting growth of *Pseudomonas aeruginosa* provided by the ceramic materials of the second embodiment of the present disclosure was in the sequence of MBG-Ag1>MBG-Ag10>MBG-Ag5.

4. The Time-kill Curves Test for *Escherichia coli* ATCC 8739

Figure 16:
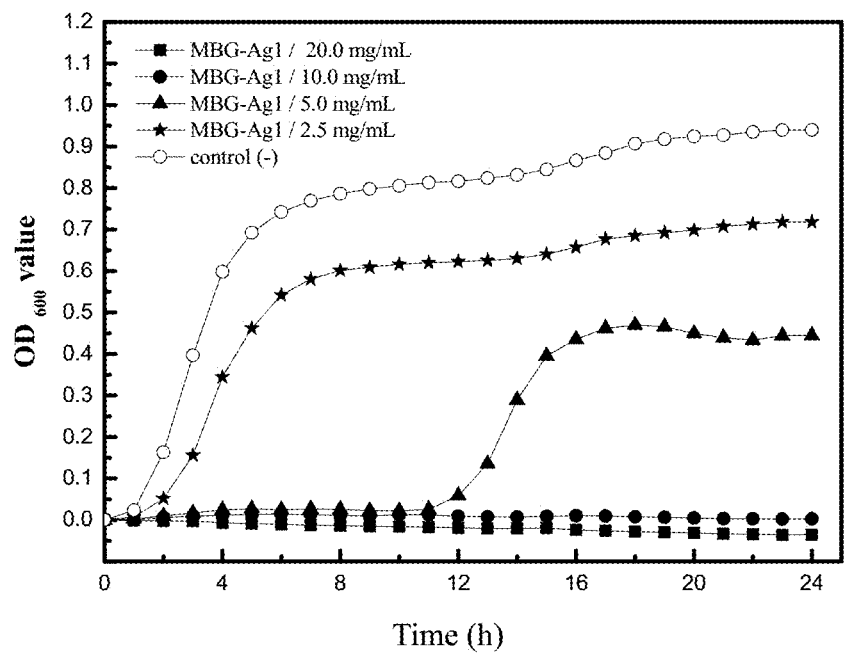
FIG. 16 is a diagram showing growth curves of time-kill curves test for *Escherichia coli* performed by adding different concentrations of the ceramic material MBG-Ag1 in a liquid culture medium in accordance with the second embodiment of the present disclosure.
Figure 17:
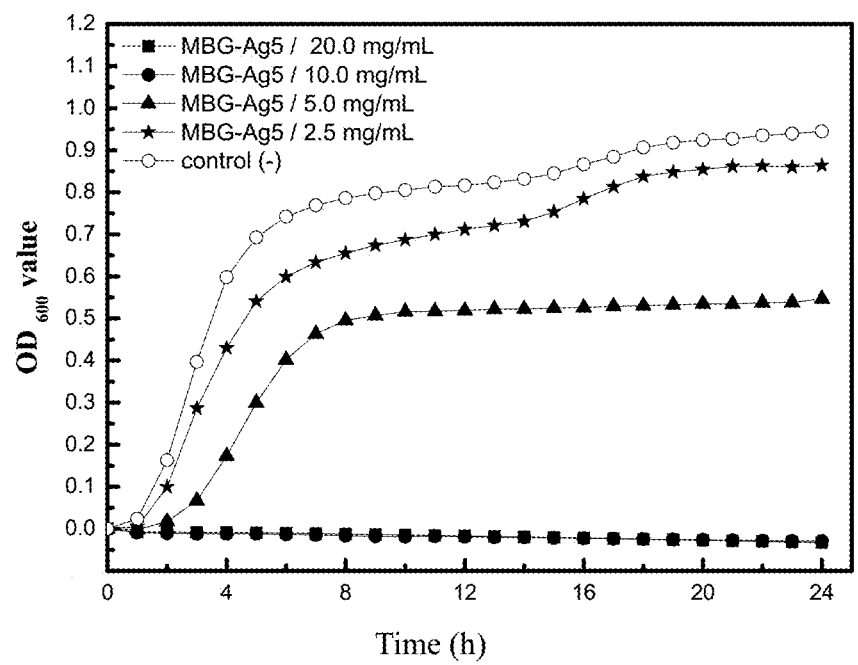
FIG. 17 is a diagram showing growth curves of time-kill curves test for *Escherichia coli* performed by adding different concentrations of the ceramic material MBG-Ag5 in a liquid culture medium in accordance with the second embodiment of the present disclosure.
Figure 18:
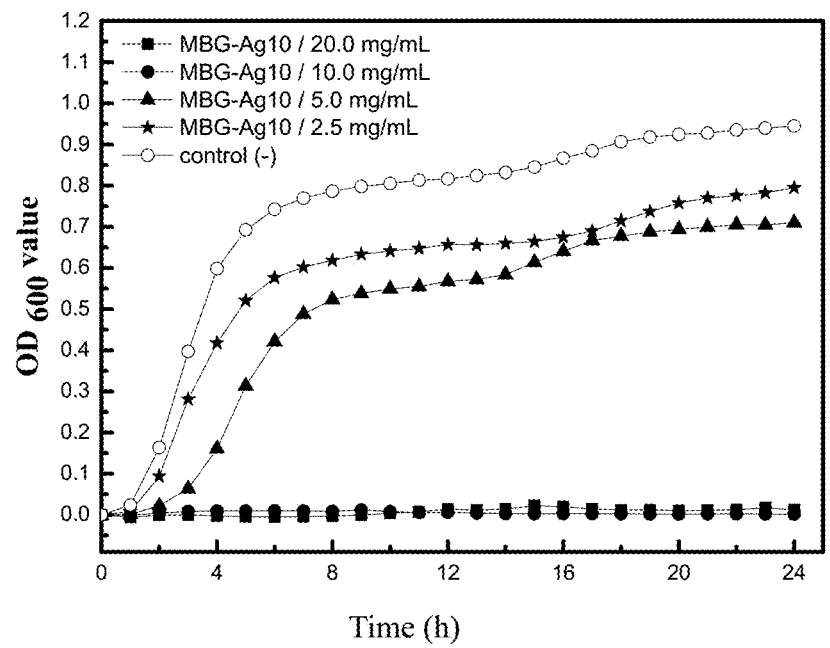
FIG. 18 is a diagram showing growth curves of time-kill curves test for *Escherichia coli* performed by adding different concentrations of the ceramic material MBG-Ag10 in a liquid culture medium in accordance with the second embodiment of the present disclosure.

FIGS. 16-18 show growth curves of time-kill curves test for *Escherichia coli* performed by adding different concentrations of the ceramic materials MBG-Ag1, MBG-Ag5 and MBG-Ag10 in a liquid culture medium in accordance with the second embodiment of the present disclosure. FIG. 16 is a diagram showing growth curves of time-kill curves test for *Escherichia coli* performed by adding different concentrations of the ceramic material MBG-Ag1 in a liquid culture medium in accordance with the second embodiment of the present disclosure. The condition to prepare the liquid culture medium included adding MBG-Ag1 in the extract solution having concentrations in ratios of 2.5, 5, 10 and 20 of the weight (in mg) of the ceramic material to the volume (in ml) of specific culture medium. It could be seen from FIG. 16 that, the extract solution had an excellent effect of inhibiting growth of the bacteria when the concentrations of MBG-Ag1 extract solution were 20 mg/mL and 10 mg/mL. The effect of inhibiting growth of the bacteria was limited when the concentration of the extract solution was 5 mg/mL, and there was a growth phenomenon of *Escherichia coli* at 12 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 17 is a diagram showing growth curves of time-kill curves test for *Escherichia coli* performed by adding different concentrations of the ceramic material MBG-Ag5 in a liquid culture medium in accordance with the second embodiment of the present disclosure. The condition to prepare the liquid culture medium included adding MBG-Ag5 in the extract solution having concentrations in ratios of 2.5, 5, 10 and 20 of the weight (in mg) of the ceramic material to the volume (in ml) of specific culture medium. It could be seen from FIG. 17 that, the extract solution had an excellent effect of inhibiting growth of the bacteria when the concentrations of MBG-Ag5 extract solution were 20 mg/mL and 10 mg/mL. The effect of inhibiting growth of the bacteria was limited when the concentration of the extract solution was 5 mg/mL, and there was a growth phenomenon of *Escherichia coli* at 2 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 18 is a diagram showing growth curves of time-kill curves test for *Escherichia coli* performed by adding different concentrations of the ceramic material MBG-Ag10 in a liquid culture medium in accordance with the second embodiment of the present disclosure. The condition to prepare the liquid culture medium included adding MBG-Ag10 in the extract solution having concentrations in ratios of 2.5, 5, 10 and 20 of the weight (in mg) of the ceramic material to the volume (in ml) of specific culture medium. It could be seen from FIG. 18 that, the extract solution had an excellent effect of inhibiting growth of the bacteria when the concentrations of MBG-Ag10 extract solution were 20 mg/mL and 10 mg/mL. The effect of inhibiting growth of the bacteria was limited when the concentration of the extract solution was 5 mg/mL, and there was a growth phenomenon of *Escherichia coli* at 2 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

Preliminary conclusion: The effect of inhibiting growth of *Escherichia coli* provided by the ceramic materials of the second embodiment of the present disclosure was in the sequence of MBG-Ag1>MBG-Ag10≈MBG-Ag5.

5. The Time-kill Curves Test for *Enterococcus faecalis* ATCC 29212

Figure 19:
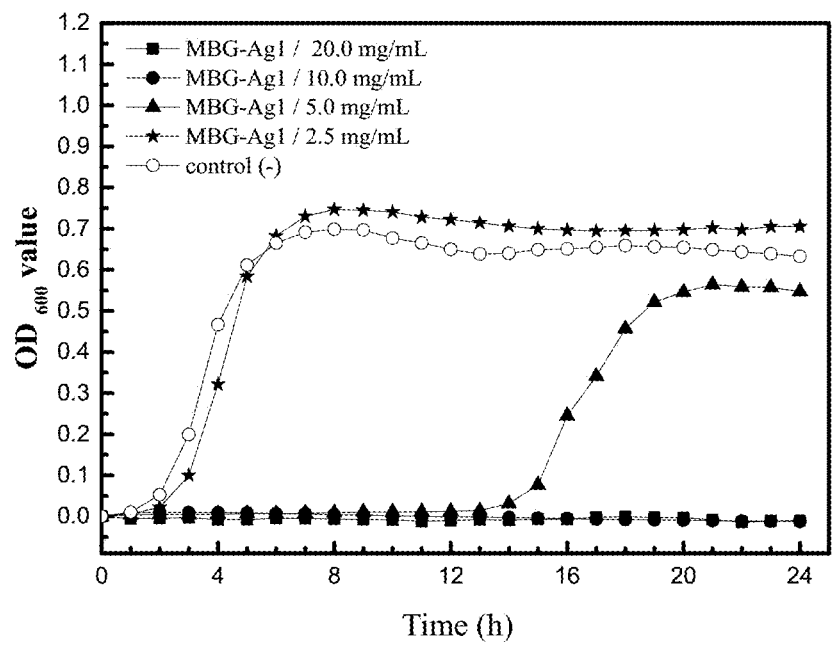
FIG. 19 is a diagram showing growth curves of time-kill curves test for *Enterococcus faecalis* performed by adding different concentrations of the ceramic material MBG-Ag1 in a liquid culture medium in accordance with the second embodiment of the present disclosure.
Figure 20:
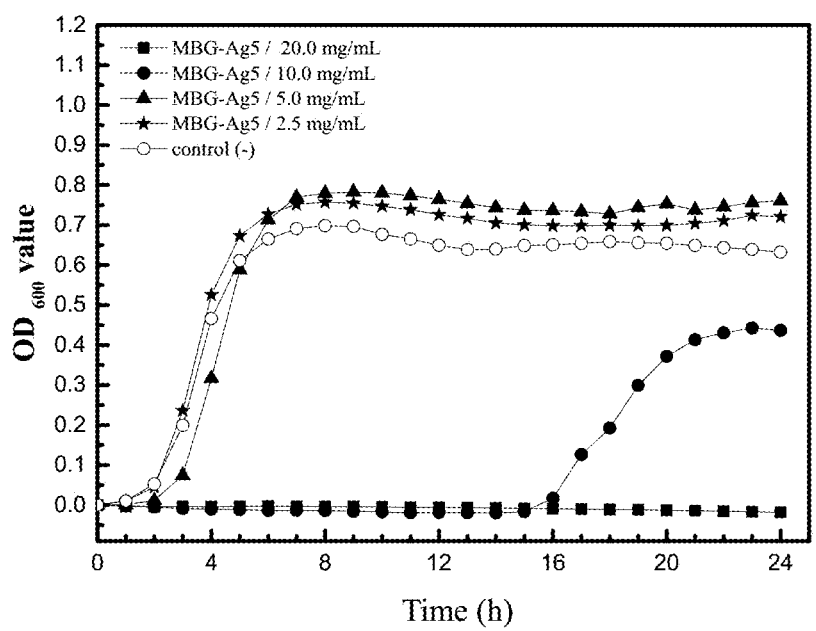
FIG. 20 is a diagram showing growth curves of time-kill curves test for *Enterococcus faecalis* performed by adding different concentrations of the ceramic material MBG-Ag5 in a liquid culture medium in accordance with the second embodiment of the present disclosure.
Figure 21:
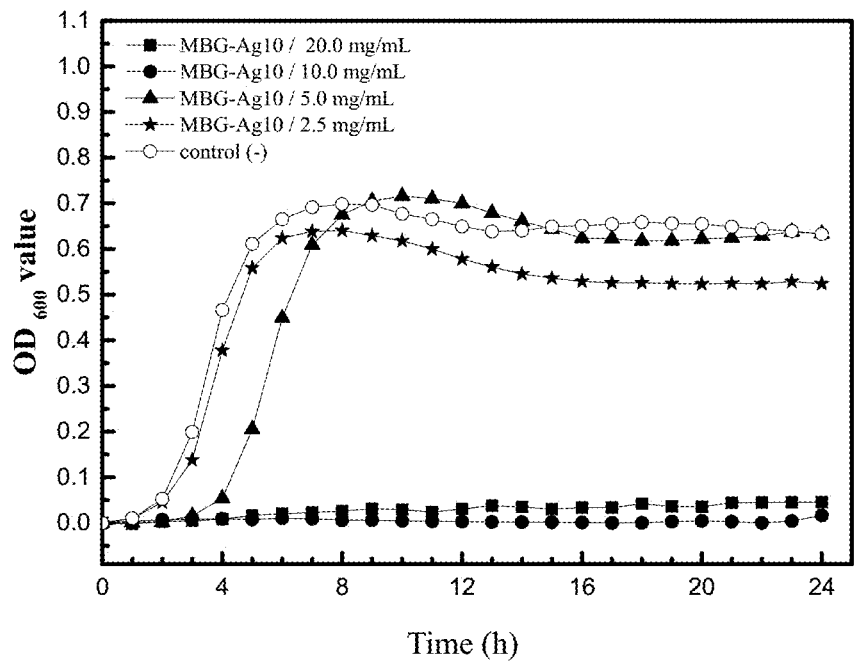
FIG. 21 is a diagram showing growth curves of time-kill curves test for *Enterococcus faecalis* performed by adding different concentrations of the ceramic material MBG-Ag10 in a liquid culture medium in accordance with the second embodiment of the present disclosure.

FIGS. 19-21 show growth curves of time-kill curves test for *Enterococcus faecalis* performed by adding different concentrations of the ceramic materials MBG-Ag1, MBG-Ag5 and MBG-Ag10 in a liquid culture medium in accordance with the second embodiment of the present disclosure. FIG. 19 is a diagram showing growth curves of time-kill curves test for *Enterococcus faecalis* performed by adding different concentrations of the ceramic material MBG-Ag1 in a liquid culture medium in accordance with the second embodiment of the present disclosure. The condition to prepare the liquid culture medium included adding MBG-Ag1 in the extract solution having concentrations in ratios of 2.5, 5, 10 and 20 of the weight (in mg) of the ceramic material to the volume (in ml) of specific culture medium. It could be seen from FIG. 19 that, the extract solution had an excellent effect of inhibiting growth of the bacteria when the concentrations of MBG-Ag1 extract solution were 20 mg/mL and 10 mg/mL. The effect of inhibiting growth of the bacteria was limited when the concentration of the extract solution was 5 mg/mL, and there was a growth phenomenon of *Enterococcus faecalis* at 13 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

FIG. 20 is a diagram showing growth curves of time-kill curves test for *Enterococcus faecalis* performed by adding different concentrations of the ceramic material MBG-Ag5 in a liquid culture medium in accordance with the second embodiment of the present disclosure. The condition to prepare the liquid culture medium included adding MBG-Ag5 in the extract solution having concentrations in ratios of 2.5, 5, 10 and 20 of the weight (in mg) of the ceramic material to the volume (in ml) of specific culture medium. It could be seen from FIG. 20 that, the extract solution had an excellent effect of inhibiting growth of the bacteria when the concentration of MBG-Ag5 extract solution was 20 mg/mL. The effect of inhibiting growth of the bacteria was limited when the concentration of the extract solution was 10 mg/mL, and there was a growth phenomenon of *Enterococcus faecalis* at 2 hours. Therefore, the minimum inhibitory concentration (MIC) was expected in the range from 10 mg/mL to 20 mg/mL. No effect of inhibiting growth of the bacteria was observed when the concentration of the extract solution was 5 mg/mL or 2.5 mg/mL.

FIG. 21 is a diagram showing growth curves of time-kill curves test for *Enterococcus faecalis* performed by adding different concentrations of the ceramic material MBG-Ag10 in a liquid culture medium in accordance with the second embodiment of the present disclosure. The condition to prepare the liquid culture medium included adding MBG-Ag10 in the extract solution having concentrations in ratios of 2.5, 5, 10 and 20 of the weight (in mg) of the ceramic material to the volume (in ml) of specific culture medium. It could be seen from FIG. 21 that, the extract solution had an excellent effect of inhibiting growth of the bacteria when the concentrations of MBG-Ag10 extract solution were 20 mg/mL and 10 mg/mL. The effect of inhibiting growth of the bacteria was limited when the concentration of the extract solution was 5 mg/mL, and there was a growth phenomenon of *Enterococcus faecalis* at 2 hours. Therefore, the minimum inhibitory concentration (MIC) was expected in the range from 5 mg/mL to 10 mg/mL. No effect of inhibiting growth of the bacteria was observed when the concentration of the extract solution was 2.5 mg/mL.

Preliminary conclusion: The effect of inhibiting growth of *Enterococcus faecalis* provided by the ceramic materials of the second embodiment of the present disclosure was in the sequence of MBG-Ag1>MBG-Ag10>MBG-Ag5.

Conclusions: All of the ceramic materials of the second embodiment in accordance with the present disclosure had the effects of inhibiting growth of the bacteria. The inhibiting effects were in the sequence of MBG-Ag1>MBG-Ag10>MBG-Ag5.

It is speculated that the possible reason for the above conclusions is that, when the ceramic material MBG-Ag1 is in an environment or system having a hydrophilic medium, the nano-scale Ag particles adsorbed on the surface of the mesoporous structure or confined in the mesoporous structure will positively release the Ag ions. When the concentration of the Ag ions achieves the saturation concentration, the Ag ions will nucleate and grow to form nano-scale Ag particles. The nano-scale Ag particles and the dissociated Ag ions which do not form the nano-scale Ag particles can destruct a cell wall of the microorganisms or form reactive oxygen species (ROS) to destruct a structure of the microorganisms. So they can achieve the effects of inhibiting growth of the microorganisms or killing the microorganisms.

The ceramic materials MBG-Ag5 and MBG-Ag10 may repeat the steps same as MBG-Ag1 in an environment or a system having the hydrophilic medium, which steps comprise releasing positively the Ag ions and when the concentration of the Ag ions achieves the saturation concentration, the Ag ions will nucleate and grow to form nano-scale Ag particles. However, the Ag concentrations of MBG-Ag5 and MBG-Ag10 are higher, the Ag ions have nucleated and grown to form the nano-scale Ag particles and further aggregated with each other in the environment or system containing a hydrophilic medium, or the phenomena of Ostwald ripening is observed. So the effects of inhibiting growth of the microorganisms or killing the microorganisms become poorer accordingly.

Therefore, MBG-Ag1 having the minimum diameter of the nano-scale Ag particles in the environment or system having the hydrophilic medium has the best effect of inhibiting the growth of the bacteria. MBG-Ag5 and MBG-Ag10 having the larger diameter of the nano-scale Ag particles in the environment or system containing the hydrophilic medium have the poor effect of inhibiting the growth of the bacteria.

Figure 22A:
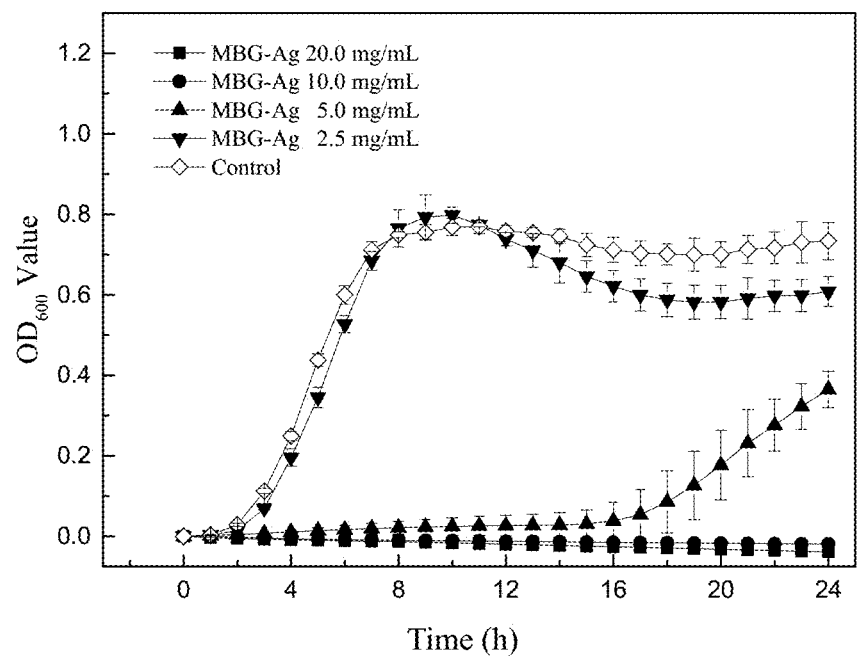
FIG. 22A is a diagram showing growth curves of time-kill curves test for *Staphylococcus aureus* performed by adding different concentrations of the ceramic material MBG-Ag in a liquid culture medium in accordance with a third embodiment of the present disclosure.
Figure 22B:
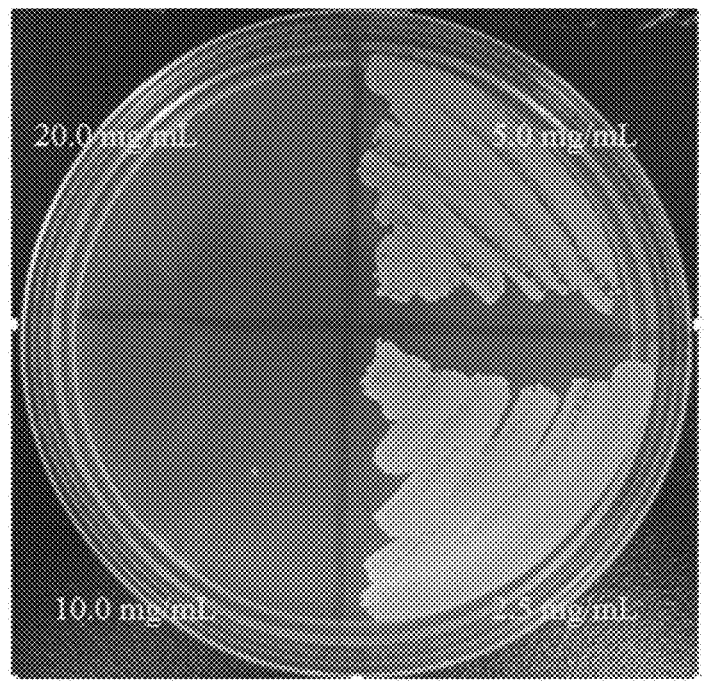
FIG. 22B is a diagram showing results of the colony-forming capacity assay for *Staphylococcus aureus* performed by adding different concentrations of the ceramic material MBG-Ag in a liquid culture medium in accordance with the third embodiment of the present disclosure.
Figure 23A:
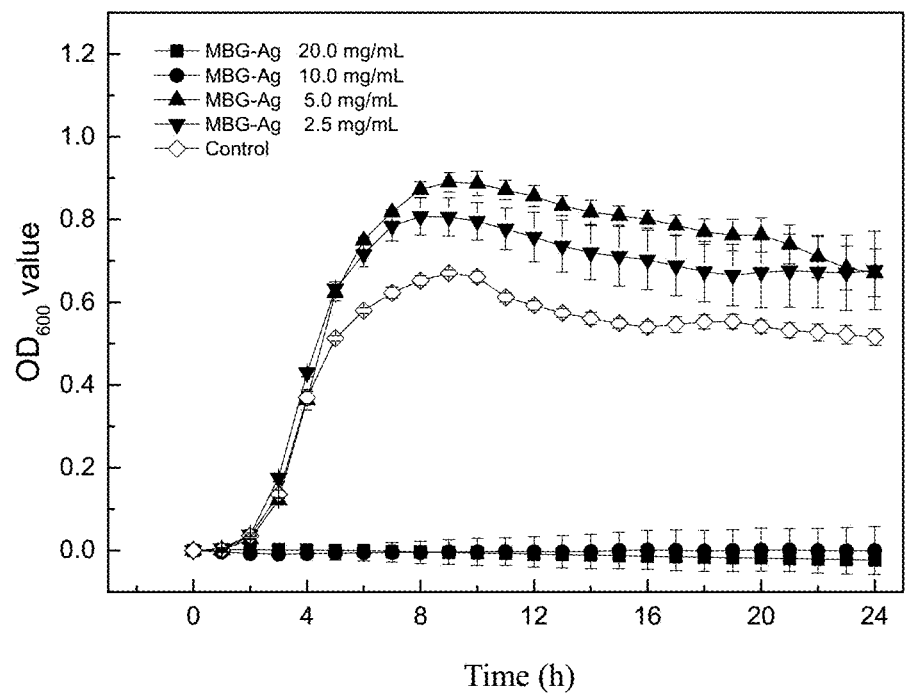
FIG. 23A is a diagram showing growth curves of time-kill curves test for *Pseudomonas aeruginosa* performed by adding different concentrations of the ceramic material MBG-Ag in a liquid culture medium in accordance with the third embodiment of the present disclosure.
Figure 23B:
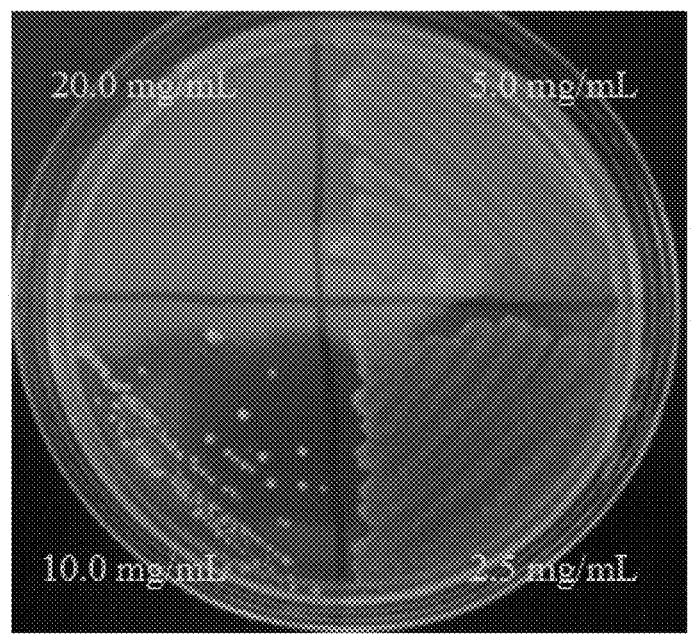
FIG. 23B is a diagram showing results of the colony-forming capacity assay for *Pseudomonas aeruginosa* performed by adding different concentrations of the ceramic material MBG-Ag in a liquid culture medium in accordance with the third embodiment of the present disclosure.
Figure 24:
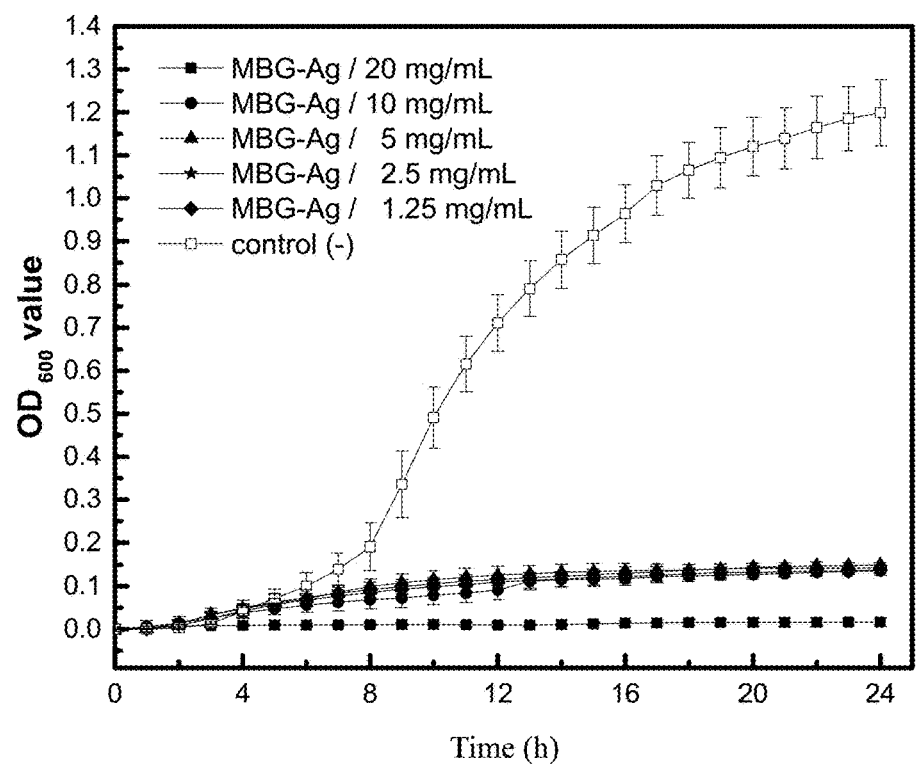
FIG. 24 is a diagram showing growth curves of time-kill curves test for *Klebsiella pneumoniae* performed by adding different concentrations of the ceramic material MBG-Ag in a liquid culture medium in accordance with the third embodiment of the present disclosure.

Third Embodiment:

The third embodiment of the present disclosure discloses a ceramic material comprising a hierarchically meso-macroporous structure and having a tissue induction property or a tissue conduction property. The ceramic material can be used for a bone filling or a bone integration material. The hierarchically meso-macroporous structure which composition includes silicon, calcium, phosphor, and oxygen with an addition of 1 mol % of Ag therein. MBG-Ag hereinafter represents the ceramic material with Si:Ca:P:Ag in the molar ratio 79:15:5:1. For completely illustrating in detail the third embodiment in accordance with the present disclosure, please refer to FIGS. 22A-24. FIGS. 22A, 23A and 24 show growth curves of time-kill curves test, which demonstrate that the nano-scale metal particles contained in the ceramic material having a hierarchically meso-macroporous structure located in an environment or a system containing a hydrophilic medium have a positive slow release effect. The nano-scale metal particles contained in the ceramic material have the effects of inhibiting growth of the microorganisms or killing the microorganisms. This test was performed in an environment or a system having a hydrophilic medium possessing the microorganisms, such as a liquid culture medium, at a temperature of 32.5±2.5° C. with or without the addition of the ceramic material having a hierarchically meso-macroporous structure of the third embodiment. After a specific cultivation time, each group of the solutions were formed, and the numbers of the microorganisms in each group were measured. The numbers of the microorganisms were calculated by measuring the turbidity of each group of the solutions. The turbidity of each solution was obtained by measuring the absorbance (or called the optical density (OD) value) at a wavelength of 600 nm ($OD_{600}$ value) using the ELISA reader. The growth curves of the test microorganisms in the environment or system were plotted with time as the horizontal axis and the optical density at 600 nm ($OD_{600}$) as the longitudinal axis. The test microorganisms can be selected from bacteria, viruses, fungi or protozoa, wherein the bacteria can be such as Methicillin-resistant *staphylococcus aureus*, *Staphylococcus aureus*, *Pseudomonas aeruginosa*, *Escherichia coli*, *Aggregatibacter actinomycetemcomnitans*, *Candida albicans*, *Klebsiella pneumnoniae*, *Enterococcus faecalis*, and so on. The fungi can be such as *Aspergillus niger*. The conditions of the liquid culture medium included adding MBG-Ag in the extract solution having concentrations in ratios of 2.5, 5, 10 and 20 of the weight (in mg) of the ceramic material to the volume (in ml) of specific culture medium, such as the cation-adjusted Mueller-Hinton broth (CAMHB). After placing in an incubator at constant temperature of 32.5±2.5° C. and extracting at 160 rpm for 24 hours, the solution was centrifuged at 3000 rpm for 5 minutes. The supernatant was drew and taken as the extract solution of the test sample. The test microorganisms were thawed and inoculated on each specific agar, and then placed in an incubator at a specific temperature for a specific period of time, the strain was swabbed with a sterile cotton swab and inoculated into each sterilized liquid culture medium (agar). The specific period of time is no more than 4 hours. A turbidimeter was used to measure the test microorganism solution and the concentration was adjusted to about $1.5 \times 10^8$ CFU/mL. The test microorganism solution was added to the 96-well microtiter plate containing the prepared extract solution. After inoculation, the final concentration of the test microorganism solution was approximately 5×10⁵ CFU/mL. After incubation at 32.5±2.5° C., the absorbance was measured once every hour until reaching 24 hours by using a spectrophotometer, and the time-kill curves were plotted to find out the minimum inhibitory concentration (MIC) of different microorganisms with respect to the ceramic material having a hierarchically meso-macroporous structure of the embodiment. The minimum inhibitory concentration (MIC) referred to the minimum concentration that could inhibit the growth of the microorganisms and was observed after culturing for 24 hours. The condition of the control group included that a liquid culture medium containing different test strains was cultured for 24 hours without adding any test liquid formed of extract solution including the ceramic material having a hierarchically meso-macroporous structure, and this control group was represented by Control (−) in subsequent descriptions.

The time-kill curves test could be used for analyzing whether the microorganisms are growing. However, the ratio of viable bacteria to dead bacteria in the test tubes could not be known from the absorbance values. Therefore, the colony-forming capacity assay analysis was necessary to further find out the minimum inhibitory concentration (MIC) and minimum bactericidal concentration (MBC) of the ceramic material. FIGS. 22B and 23B are diagrams showing test results of the colony-forming capacity assay. The purpose was to study the colony-forming capacity of the bacteria in the environment containing the antibacterial material. The assay steps included inoculating the microorganisms with a concentration of 10⁵-10⁶ CFU/mL to the ceramic material MBG-Ag. After incubation at 32.5±2.5° C. in the incubator for 24 hours, the cultivation solution was swabbed with a sterile cotton swab and was thereby coated on the tryptic soy broth (TSA) agar. After placing in an incubator at a temperature of 32.5±2.5° C. for 24 hours, the results of the minimum bactericidal concentration (MBC) for the ceramic material MBG-Ag having a hierarchically meso-macroporous structure of the third embodiment in accordance with the present disclosure with respect to different microorganisms were observed. The minimum bactericidal concentration (MBC) was the lowest concentration required to kill 99.9%, which meant to reduce three magnitudes, of the test microorganisms.

The results of the time-kill curves test and the colony-forming capacity assay, as shown in FIGS. 22A-24.

1. The Time-kill Curves Test and the Colony-forming Capacity Assay for *Staphylococcus aureus* ATCC29213

FIG. 22A is a diagram showing growth curves of time-kill curves test for *Staphylococcus aureus* performed by adding different concentrations of the ceramic material MBG-Ag in a liquid culture medium in accordance with the third embodiment of the present disclosure. It could be seen from the curve of the control group in FIG. 22A that *Staphylococcus aureus* was in a growth phase during the first 8 hours, in which the absorbance was rapidly increased because of the fast breeding. After 8 hours, the *Staphylococcus aureus* was saturated and achieved a plateau phase and a recession phase, in which the absorbance was slightly decreased. When the concentration of the MBG-Ag extract solution was 2.5 mg/mL, the absorbance increased rapidly, indicating that it could not inhibit the growth of *Staphylococcus aureus*. When the concentration of the MBG-Ag extract solution increased to 5 mg/mL, it had an excellent effect of inhibiting growth of *Staphylococcus aureus* during the first 15 hours. However, at the 16th hour, the absorbance began to rise, indicating that the antibacterial effect was weakened and the growth of *Staphylococcus aureus* could not be inhibited continuously. When the concentration of MBG-Ag extract solution was 10 mg/mL or 20 mg/mL, the absorbance showed a flat trend during the 24-hour test period, indicating that it could effectively inhibit the growth of *Staphylococcus aureus*. Therefore, the minimum inhibitory concentration (MIC) was expected in the range from 5 mg/mL to 10 mg/mL.

FIG. 22B is a diagram showing a test result of the colony-forming capacity assay for *Staphylococcus aureus* performed by adding different concentrations of the ceramic material MBG-Ag in a liquid culture medium in accordance with the third embodiment of the present disclosure. It could be seen from FIG. 22B that, when concentration of the MBG-Ag extract solution was 2.5 mg/mL or 5 mg/mL, a large range of *Staphylococcus aureus* colonies appeared in the liquid culture medium, indicating that it could not inhibit the growth of *Staphylococcus aureus* in the concentrations. When the concentration of MBG-Ag extract solution was 10 mg/mL or 20 mg/mL, the liquid culture medium was free of *Staphylococcus aureus* colonies. The extract solution in the concentrations not only inhibited the growth of the bacteria but also achieved the effect of killing the bacteria. Therefore, the minimum bactericidal concentration (MBC) was expected in the range from 5 mg/mL and 10 mg/mL.

Preliminary conclusion: The minimal inhibitory concentration (MIC) of the ceramic material MBG-Ag against *Staphylococcus aureus* was in the range from 5 mg/mL to 10 mg/mL, and the minimum bactericidal concentration (MBC) of the ceramic material MBG-Ag against *Staphylococcus aureus* was in the range from 5 mg/mL to 10 mg/mL in accordance with the third embodiment of the present disclosure.

2. The Time-kill Curves Test and Colony-forming Capacity Assay of *Pseudomonas aeruginosa* ATCC 27853

FIG. 23A is a diagram showing growth curves of time-kill curves test for *Pseudomonas aeruginosa* performed by adding different concentrations of the ceramic material MBG-Ag in a liquid culture medium in accordance with the third embodiment of the present disclosure. It could be seen from the curve of the control group in FIG. 23A that *Pseudomonas aeruginosa* was in a growth phase during the first 10 hours, in which the absorbance was rapidly increased because of the fast breeding. After 10 hours, the *Pseudomonas aeruginosa* was saturated and achieved a plateau phase and a recession phase, in which the absorbance was slightly decreased. When the concentration of the MBG-Ag extract solution was 2.5 mg/mL or 5 mg/mL, the absorbance increased rapidly, indicating that it could not inhibit the growth of *Pseudomonas aeruginosa*. When the concentration of MBG-Ag extract solution was 10 mg/mL or 20 mg/mL, the absorbance showed a flat trend during the 24-hour test period, indicating that it could effectively inhibit the growth of *Pseudomonas aeruginosa*. Therefore, the minimum inhibitory concentration (MIC) was expected in the range from 5 mg/mL to 10 mg/mL.

FIG. 23B is a diagram showing a test result of the colony forming ability for *Pseudomonas aeruginosa* performed by adding different concentrations of the ceramic material MBG-Ag in a liquid culture medium in accordance with the third embodiment of the present disclosure. It could be seen from FIG. 23B that, when concentration of the MBG-Ag extract solution was 2.5 mg/mL or 5 mg/mL, a large range of *Pseudomonas aeruginosa* colonies appeared in the liquid culture medium, indicating that it could not inhibit the growth of *Pseudomonas aeruginosa* in the concentrations. When the concentration of MBG-Ag extract solution was 10 mg/mL, only a few of *Pseudomonas aeruginosa* colonies was observed in the liquid culture medium, indicating that the extract solution in this concentration could inhibit the growth of the bacteria, but it did not achieve the effect of killing the bacteria. When the concentration of MBG-Ag extract solution was 20 mg/mL, the liquid culture medium was free of *Pseudomonas aeruginosa* colonies. The extract solution in the concentration not only inhibited the growth of the bacteria but also achieved the effect of killing the bacteria. Therefore, the minimum bactericidal concentration (MBC) was expected in the range from 10 mg/mL and 20 mg/mL.

Preliminary conclusion: The minimal inhibitory concentration (MIC) of the ceramic material MBG-Ag against *Pseudomonas aeruginosa* was in the range from 5 mg/mL to 10 mg/mL, and the minimum bactericidal concentration (MBC) of the ceramic material MBG-Ag against *Pseudomonas aeruginosa* was in the range from 10 mg/mL to 20 mg/mL in accordance with the third embodiment of the present disclosure.

3. The Time-kill Curves Test for *Klebsiella pneumoniae* ATCC 700603

FIG. 24 is a diagram showing growth curves of time-kill curves test for *Klebsiella pneumoniae* performed by adding different concentrations of the ceramic material MBG-Ag in a liquid culture medium in accordance with the third embodiment of the present disclosure. It can be seen from the curve of the control group in FIG. 24 that *Klebsiella pneumoniae* was in a growth phase during the 24-hour test period, in which the absorbance was rapidly increased because of the fast breeding. When the concentration of MBG-Ag extract solution was greater than or equal to 2.5 mg/mL, the absorbance showed a flat trend during the 24-hour test period, indicating that it could effectively inhibit the growth of *Klebsiella pneumoniae*. Therefore, the minimum inhibitory concentration (MIC) was expected to be less than 2.5 mg/mL.

Preliminary conclusion: The minimal inhibitory concentration (MIC) of the ceramic material MBG-Ag against *Klebsiella pneumoniae* was less than 2.5 mg/mL in accordance with the third embodiment of the present disclosure.

Conclusions: All of the ceramic materials of the third embodiment in accordance with the present disclosure not only have the effect of inhibiting the growth of the test microorganisms but also have the effect of killing the microorganisms.

In the above embodiments, the ceramic material comprising a hierarchically meso-macroporous structure has the following features. 1. The diameters of the nano-scale metal particles that can be controlled are no more than 10 nm. 2. The nano-scale metal particles can avoid directly contacting with the human body. 3. The ceramic material has the positive slow release effect of the nano-scale metal particles. 4. The ceramic material can be mass-produced. 5. The ceramic material can be a powder form and can be immersed, diluted, and reused.

In the above embodiments, the hydrophilic medium can be, for example, a biological body fluid, a water-containing solution, an alcohol, a human blood, a de-ionized water, a microbiological culture medium (Agar), and a simulated body fluid. The diameter of the nano-scale metal particles is no more than 10 nm; and the material of the nano-scale metal particles can be selected from gold, silver, copper and zinc, or combinations thereof, or from other groups of metal that have the property of inhibiting growth of the microorganisms or killing the microorganisms.

In the above embodiments, the positive slow release effect is free from additionally applied one selected from a group consisting of an energy, a heat, and a catalyst on the ceramic material, environment, or system.

In the above embodiments, the method for manufacturing the ceramic material comprises parts of the steps of the sol-gel technique.

In the above embodiments, a three-dimensional macroporous configuration template is provided in the method for manufacturing the ceramic material. The advantage thereof is that, its macroporous structure can provide channels to remove the template surfactant of forming the mesoporous structure during the ceramic material is treated at a temperature of no less than 400° C. The residual carbons in the final synthesized products resulted from the prior manufacturing method can be prevented.

Embodiments

1. A method for manufacturing a ceramic material having a hierarchically meso-macroporous structure and nano-scale metal particles, the method comprising steps of: providing and mixing raw materials or precursors thereof to form the hierarchically meso-macroporous structure which composition at least includes silicon and oxygen, a metal material or a precursor thereof, and a template surfactant of forming a mesoporous structure to form a mixture; synthesizing the mixture to form an initial gel by sol-gel technique; providing a three-dimensional macroporous configuration template; immersing the three-dimensional macroporous configuration template in the initial gel at least once; and removing the three-dimensional macroporous configuration template and the template surfactant of forming the mesoporous structure during a heat treatment at a temperature of no less than 400° C. to form the ceramic material.

2. The method of Embodiment 1, wherein the ceramic material has the hierarchically meso-macroporous structure comprising a plurality of macropores and a wall having a plurality of arranged mesopores, and the plurality of macropores are separated by the wall.

3. The method of Embodiments 1 and 22, wherein the wall is formed from the raw materials or the precursors thereof to form the hierarchically meso-macroporous structure, the nano-scale metal particles are formed form the metal material or the precursor thereof, and the nano-scale metal particles are confined in at least one of the plurality of arranged mesopores and have a positive slow release effect from the at least one of the plurality of arranged mesopores.

4. The method of Embodiments 1-3, wherein the positive slow release effect of the nano-scale metal particles is defined as a concentration of the nano-scale metal particles releasing positively metal ions of at least 2 ppm within one hour and the metal ions keep releasing continuously for a period of at least 24 hours at room temperature when the ceramic material is located in an environment or a system containing a hydrophilic medium.

5. The method of Embodiments 1-4, wherein the hydrophilic medium is one selected from a group consisting of a biological body fluid, a water-containing solution, an alcohol, a human blood, a de-ionized water, a microbiological culture medium, a simulated body fluid, and combinations thereof.

6. The method of Embodiments 1-5, wherein at least one of the plurality of the macropores has a pore diameter of 200-700 μm, and at least one of the plurality of arranged mesopores has a pore diameter of 2-20 nm.

7. The method of Embodiments 1-6, wherein when a total quantity of the raw materials or the precursors thereof to form the hierarchically meso-macroporous structure is $M_1$ mole and a quantity of the metal material or the precursor thereof is $M_{metal}$ mole, and the $M_{metal}$ is 0-10% of the $M_1$.
8. The method of Embodiments 1-7, wherein the $M_{metal}$ is 1% of the $M_1$.
9. The method of Embodiments 1-8, wherein the ceramic material is a powder form, and a specific surface area of the powder form is 300-700 $m^2/g$.
10. The method of Embodiments 1-9, wherein the three-dimensional macroporous configuration template is a porous organism or a synthetic porous object, the porous organism is a natural sponge, and the synthetic porous object is a polyurethane foam or a macroporous polylactic acid configuration.
11. The method of Embodiments 1-10, further comprising a step of providing a stabilizer in the mixture to reduce an aggregation or oxidization possibility of the metal material or the precursor thereof.
12. The method of Embodiments 1-11, wherein the ceramic material has a biocompatibility, and the biocompatibility is nontoxic to cells or tissues of an organism.
13. The method of Embodiments 1-12, wherein the nano-scale metal particles have a property of inhibiting growth of microorganisms or killing the microorganisms, and the nano-scale metal particles have a diameter of no more than 10 nm.
14. The method of Embodiments 1-13, wherein the nano-scale metal particles have a material selected from a group consisting of gold, silver, copper, zinc, and combinations thereof.
15. The method of Embodiments 1-14, wherein the raw materials or the precursors thereof to form the hierarchically meso-macroporous structure further comprise one selected from a group consisting of phosphor, calcium, and a combination thereof.
16. A ceramic material, comprising: a hierarchically meso-macroporous structure which composition at least includes silicon and oxygen, wherein the hierarchically meso-macroporous structure comprises a plurality of macropores and a wall having a plurality of arranged mesopores, and the plurality of macropores are separated by the wall; and nano-scale metal particles confined in at least one of the plurality of arranged mesopores, wherein the nano-scale metal particles have a positive slow release effect from the at least one of the plurality of arranged mesopores.
17. The ceramic material of Embodiment 16, wherein the positive slow release effect of the nano-scale metal particles is defined as a concentration of the nano-scale metal particles releasing positively metal ions of at least 2 ppm within one hour and the metal ions keep releasing continuously for a period of at least 24 hours at room temperature when the ceramic material is located in an environment or a system containing a hydrophilic medium.
18. The ceramic material of Embodiments 16 and 17, wherein the hydrophilic medium is one selected from a group consisting of a biological body fluid, a water-containing solution, an alcohol, a human blood, a de-ionized water, a microbiological culture medium, a simulated body fluid, and combinations thereof.
19. The ceramic material of Embodiments 16-18, wherein the positive slow release effect is free from additionally applied one selected from a group consisting of an energy, a heat, and a catalyst.
20. The ceramic material of Embodiments 16-19, wherein the nano-scale metal particles have a property of inhibiting growth of microorganisms or killing the microorganisms, and the nano-scale metal particles have a diameter of no more than 10 nm.
21. The ceramic material of Embodiments 16-20, wherein the ceramic material has a biocompatibility, and the biocompatibility is nontoxic to cells or tissues of an organism.
22. The ceramic material of Embodiments 16-21, wherein the composition of the hierarchically meso-macroporous structure further comprises one selected from a group consisting of phosphor, calcium, and a combination thereof.
23. The ceramic material of Embodiments 16-23, wherein the ceramic material has a tissue induction property or a tissue conduction property.
24. The ceramic material of Embodiments 16-23, wherein a quantity of the nano-scale metal particles is no more than 10% of a total quantity of the composition to form the hierarchically meso-macroporous structure, wherein the quantity of the nano-scale metal particles and the total quantity of the composition to form the hierarchically meso-macroporous structure are expressed in moles.
25. The ceramic material of Embodiments 16-24, wherein the quantity of the nano-scale metal particles is about 1% of the total quantity of the composition to form the hierarchically meso-macroporous structure.
26. The ceramic material of Embodiments 16-25, wherein at least one of the plurality of the macropores has a pore diameter of 200-700 μm, and at least one of the plurality of the arranged mesopores has a pore diameter of 2-20 nm.
27. The ceramic material of Embodiments 16-26, wherein the nano-scale metal particles have a material selected from a group consisting of gold, silver, copper, zinc, and combinations thereof.
28. A system containing a hydrophilic medium and microorganisms of a first quantity A1 colony-forming unit (CFU), adding a ceramic material in the system, the microorganisms have a second quantity A2 CFU after a specific period of time, wherein the ceramic material comprising: a hierarchically meso-macroporous structure which composition at least includes silicon and oxygen, wherein the hierarchically meso-macroporous structure comprises a plurality of macropores and a wall having a plurality of arranged mesopores, and the plurality of macropores are separated by the wall; and nano-scale metal particles confined in at least one of the plurality of arranged mesopores, wherein the nano-scale metal particles have a positive slow release effect from the at least one of the plurality of arranged mesopores, wherein the A2 is no more than the A1.
29. The system of Embodiment 28, wherein the microorganisms are one selected from a group consisting of bacteria, viruses, fungi, and protozoa.
30. The system of Embodiments 28-29, wherein the system is one selected from a group consisting of a biological cell, a biological tissue, a biological organ, a cosmetic, a drug, a medical device, and a biomedical material.
31. The system of Embodiments 28-30, wherein the hydrophilic medium is one selected from a group consisting of a biological body fluid, a water-containing solution, an alcohol, a human blood, a de-ionized water, a microbiological culture medium, a simulated body fluid, and combinations thereof.
32. The system of Embodiments 28-31, wherein the specific period of time is no more than 4 hours.

33. The system of Embodiments 28-32, wherein the positive slow release effect of the nano-scale metal particles is defined as a concentration of the nano-scale metal particles releasing positively metal ions of at least 2 ppm within one hour and the metal ions keep releasing continuously for a period of at least 24 hours at room temperature when the ceramic material is located in an environment or a system containing a hydrophilic medium.

34. The system of Embodiments 28-33, wherein the nano-scale metal particles have a property of inhibiting growth of the microorganisms or killing the microorganisms, and the nano-scale metal particles have a diameter of no more than 10 nm.

35. The system of Embodiments 28-34, wherein at least one of the plurality of the macropores has a pore diameter of 200-700 μm, and at least one of the plurality of the arranged mesopores has a pore diameter of 2-20 nm 36. The system of Embodiments 28-35, wherein a quantity of the nano-scale metal particles is no more than 10% of a total quantity of the composition to form the hierarchically meso-macroporous structure, wherein the quantity of the nano-scale metal particles and the total quantity of the composition to form the hierarchically meso-macroporous structure are expressed in moles.

While the present disclosure has been described in terms of what is presently considered to be the most practical and preferred embodiments, it is to be understood that the present disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for manufacturing a ceramic material having a hierarchically meso-macroporous structure and nano-scale metal particles, the method comprising steps of:
    providing and mixing raw materials or precursors thereof to form the hierarchically meso-macroporous structure which composition at least includes silicon and oxygen, a metal material or a precursor thereof, and a template surfactant of forming a mesoporous structure to form a mixture;
    synthesizing the mixture to form an initial gel by sol-gel technique;
    providing a three-dimensional macroporous configuration template;
    immersing the three-dimensional macroporous configuration template in the initial gel at least once; and
    removing the three-dimensional macroporous configuration template and the template surfactant of forming the mesoporous structure during a heat treatment at a temperature of no less than 400° C. to form the ceramic material, wherein when a total quantity of the raw materials or the precursors thereof is $M_1$ mole, a quantity of the silicon included in the raw material or the precursor thereof is $M_{Si}$ mole, and a quantity of the metal material or the precursor thereof is $M_{metal}$ mole, the $M_{Si}$, is at least 70% of the $M_1$ and the $M_{metal}$ is 0-10% of the $M_1$.

2. The method according to claim 1, wherein the ceramic material has the hierarchically meso-macroporous structure comprising a plurality of macropores and a wall having a plurality of arranged mesopores, and the plurality of macropores are separated by the wall.

3. The method according to claim 2, wherein the wall is formed from the raw materials or the precursors thereof to form the hierarchically meso-macroporous structure, the nano-scale metal particles are formed form the metal material or the precursor thereof, and the nano-scale metal particles are confined in at least one of the plurality of arranged mesopores and have a positive slow release effect from the at least one of the plurality of arranged mesopores.

4. The method according to claim 3, wherein the positive slow release effect of the nano-scale metal particles is defined as a concentration of the nano-scale metal particles releasing positively metal ions of at least 2 ppm within one hour and the metal ions keep releasing continuously for a period of at least 24 hours at room temperature when the ceramic material is located in an environment or a system containing a hydrophilic medium.

5. The method according to claim 4, wherein the hydrophilic medium is one selected from a group consisting of a biological body fluid, a water-containing solution, an alcohol, a human blood, a de-ionized water, a microbiological culture medium, a simulated body fluid, and combinations thereof.

6. The method according to claim 2, wherein at least one of the plurality of the macropores has a pore diameter of 200-700 μm, and at least one of the plurality of arranged mesopores has a pore diameter of 2-20 nm.

7. The method according to claim 1, wherein the $M_{metal}$ is 1% of the $M_1$.

8. The method according to claim 1, wherein the ceramic material is a powder form, and a specific surface area of the powder form is 300-700 $m^2/g$.

9. The method according to claim 1, wherein the three-dimensional macroporous configuration template is a porous organism or a synthetic porous object, the porous organism is a natural sponge, and the synthetic porous object is a polyurethane foam or a macroporous polylactic acid configuration.

10. The method according to claim 1, further comprising a step of providing a stabilizer in the mixture to reduce an aggregation or oxidization possibility of the metal material or the precursor thereof.

11. The method according to claim 1, wherein the ceramic material has a biocompatibility, and the biocompatibility is nontoxic to cells or tissues of an organism.

12. The method according to claim 1, wherein the nano-scale metal particles have a property of inhibiting growth of microorganisms or killing the microorganisms, and the nano-scale metal particles have a diameter of no more than 10 nm.

13. The method according to claim 1, wherein the nano-scale metal particles have a material selected from a group consisting of gold, silver, copper, zinc, and combinations thereof.

14. The method according to claim 1, wherein the raw materials or the precursors thereof to form the hierarchically meso-macroporous structure further comprise one selected from a group consisting of phosphor, calcium, and a combination thereof.

* * * * *